US012344780B2

(12) United States Patent
Belisle et al.

(10) Patent No.: US 12,344,780 B2
(45) Date of Patent: Jul. 1, 2025

(54) POLYMER DOTS

(71) Applicant: BIO-RAD LABORATORIES, INC., Hercules, CA (US)

(72) Inventors: Christopher Belisle, Walnut Creek, CA (US); Praveena D. Garimella, Lafayette, CA (US); Leila Amery Ranis, Pinole, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 635 days.

(21) Appl. No.: 16/987,441

(22) Filed: Aug. 7, 2020

(65) Prior Publication Data

US 2021/0040382 A1   Feb. 11, 2021

Related U.S. Application Data

(60) Provisional application No. 62/884,706, filed on Aug. 9, 2019.

(51) Int. Cl.
| | | |
|---|---|---|
| *C09K 11/02* | (2006.01) | |
| *C09K 11/06* | (2006.01) | |
| *G01N 33/545* | (2006.01) | |
| *B82Y 20/00* | (2011.01) | |
| *B82Y 40/00* | (2011.01) | |

(52) U.S. Cl.
CPC ............. *C09K 11/02* (2013.01); *C09K 11/06* (2013.01); *G01N 33/545* (2013.01); *B82Y 20/00* (2013.01); *B82Y 40/00* (2013.01)

(58) Field of Classification Search
CPC ......... B82Y 20/00; B82Y 30/00; B82Y 40/00; C09K 11/02; C09K 11/06; G01N 33/545; G01N 33/582; G01N 33/585
See application file for complete search history.

(56) References Cited

U.S. PATENT DOCUMENTS

| | | | |
|---|---|---|---|
| 5,723,218 A | 3/1998 | Haugland et al. | |
| 6,383,500 B1 | 5/2002 | Wooley et al. | |
| 6,649,138 B2 | 11/2003 | Adams et al. | |
| 7,186,358 B2 | 3/2007 | McCulloch et al. | |
| 7,217,770 B2 | 5/2007 | Seo et al. | |
| 7,547,757 B2 | 6/2009 | Liu et al. | |
| 8,067,506 B2 | 11/2011 | Chen et al. | |
| 9,382,473 B2 | 7/2016 | Chiu et al. | |
| 9,797,840 B2 | 10/2017 | Chiu et al. | |
| 9,810,693 B2 | 11/2017 | Chiu et al. | |
| 2002/0045045 A1 | 4/2002 | Williams et al. | |
| 2004/0033345 A1 | 2/2004 | Dubertret et al. | |
| 2006/0063859 A1 | 3/2006 | Guan | |
| 2008/0033146 A1* | 2/2008 | Liu ............ | H10K 85/115 528/398 |
| 2010/0055189 A1 | 3/2010 | Hubbell et al. | |
| 2010/0311903 A1 | 12/2010 | Rajagopalan | |
| 2010/0330368 A1 | 12/2010 | Prud'homme et al. | |
| 2012/0282632 A1 | 11/2012 | Chiu et al. | |
| 2014/0350183 A1 | 11/2014 | Chiu et al. | |
| 2015/0056142 A1 | 2/2015 | Tao et al. | |
| 2015/0102330 A1* | 4/2015 | Carter ............ | H10K 85/115 438/46 |
| 2016/0018395 A1 | 1/2016 | Chiu et al. | |
| 2016/0018405 A1 | 1/2016 | Chiu | |
| 2016/0131659 A1 | 5/2016 | Chiu et al. | |
| 2016/0161475 A1 | 6/2016 | Chiu et al. | |
| 2016/0216271 A1 | 7/2016 | Li et al. | |
| 2017/0003293 A1 | 1/2017 | Chiu et al. | |
| 2017/0266323 A1 | 9/2017 | Tao et al. | |
| 2019/0023834 A1 | 1/2019 | McCairn et al. | |
| 2019/0106542 A1 | 4/2019 | Chiu et al. | |

FOREIGN PATENT DOCUMENTS

| | | |
|---|---|---|
| JP | 2019511455 | 4/2019 |
| WO | WO 00/53656 * | 9/2000 |
| WO | 2008121949 A1 | 10/2008 |
| WO | 2008124639 A2 | 10/2008 |
| WO | 2011057295 A2 | 5/2011 |
| WO | 2011087521 A1 | 7/2011 |
| WO | WO 2017/125456 | 7/2017 |

OTHER PUBLICATIONS

A printout retrieved from https://broadpharm.com/product/bp-23796 on Jun. 9, 2023.*
Zhang et al., "Highly luminescent, fluorinated semiconducting polymer dots for cellular imaging and analysis," Chem. Commun., 2013, vol. 49, No. 74, pp. 8256-8258.*
A printout retrieved on Oct. 30, 2023.*
Rong et al., "Multicolor Fluorescent Semiconducting Polymer Dots with Narrow Emissions and High Brightness," ACS Nano, 2013, vol. 7, No. 1, pp. 376-384.*
Ding et al. "Bright Far-Red/Near-Infrared Conjugated Polymer Nanoparticles for In Vivo Bioimaging," Small, 2013, vol. 9(18) pp. 3093-3102, published online on Apr. 26, 2013, URL: https://doi.org/10.1002/smll.201300171.

(Continued)

*Primary Examiner* — Galina M. Yakovleva
(74) *Attorney, Agent, or Firm* — Saliwanchik, Lloyd & Eisenschenk

(57) ABSTRACT

Polymer dots comprising a functionalized fluorescent polymer and an amphiphilic molecule are provided.

15 Claims, 5 Drawing Sheets

(56) References Cited

OTHER PUBLICATIONS

Feng et al. "Ultrasmall Conjugated Polymer Nanoparticles with High Specificity for Targeted Cancer Cell Imaging," Adv. Sci., May 1, 2017, vol. 4, 1600407, pp. 1-8.

Fernando et al. "The relative brightness of PEG lipid-conjugated polymer nanoparticles as fluid-phase markers in live cells." Anal. Bioanal. Chem. Dec. 2012; 404(10), pp. 3003-3014. doi:10.1007/s00216-012-6441-5.

Kandel et al. "Incorporating Functionalized Polyethylene Glycol Lipids into Reprecipitated Conjugated Polymer Nanoparticles for Bioconjugation and Targeted Labeling of Cells," Nanoscale, Mar. 2011, vol. 3, No. 3, pp. 1037-1045. URL: https://doi.org/10.1039/c0nr00746c.

Kandel, Prakash. Passivation and Functionalization of Conjugated Polymer Nanoparticles With Head Group Modified Phospholipids and Proteins. 2014. Clemson U, PhD dissertation.

Khanbeigi et al. "Surface Chemistry of Photoluminescent F8BT Conjugated Polymer Nanoparticles Determines Protein Corona Formation and Internalization by Phagocytic Cells," Biomacromolecules, Jan. 15, 2015, vol. 16, 733-742. URL: https://doi.org/10.1021/bm501649y.

Li et al. "Highly emissive PEG-encapsulated conjugated polymer nanoparticles," Nanoscale, 2012, vol. 4, pp. 5694-5702. URL: https://doi.org/10.1039/C2NR31267K.

International Search Report and Written Opinion in International Application No. PCT/US2020/045307, Oct. 27, 2020, pp. 1-13.

Extended European Search Report in European Application No. 20852998.2, Aug. 1, 2023, pp. 1-7.

\* cited by examiner

POLYMER DOTS

CROSS-REFERENCE TO RELATED APPLICATION

This application claims the benefit of U.S. Provisional Application 62/884,706 filed on Aug. 9, 2019 which is hereby incorporated by reference in its entirety.

BACKGROUND

Due to their high brightness and photostability over conventional organic dyes, nanoparticle-based fluorescent probes such as quantum dots and polymer-based dots (or polymer dots) are used in a variety of fluorescence-based techniques to study biological systems. However, inorganic quantum dots can be degraded by reactive oxygen species, releasing toxic heavy metals. Use of quantum dots is therefore limited to ex vivo applications. Fluorescent polymer dots do not have heavy metals that can leach out into solution and can therefore be used in in vivo applications. To be used in biological systems, fluorescent probes are conjugated to proteins (e.g. antibodies) through a functional group on the surface of the probe. For polymer-based nanoparticles, the polymers used to make the nanoparticle are hydrophobic and may not always have functional groups on the surface of the particle to which proteins can be attached. One approach used to functionalize the surface of the polymer dot is to apply a hydrophilic coating to the surface of the polymer dot. The hydrophilic coating has a hydrophilic functional group(s) to which protein can be conjugated.

SUMMARY

Polymer dots, methods of preparing polymer dots and bioconjugates of such polymer dots are provided.

In an embodiment, the polymer dot comprises a fluorescent polymer having hydrophobic regions and hydrophilic regions, the hydrophilic regions having a hydrophilic functional group; and an amphiphilic molecule having hydrophobic regions and hydrophilic regions, wherein the hydrophilic functional group is accessible for conjugation. In some embodiments, the hydrophobic regions of the fluorescent polymer and the amphiphilic molecule are embedded in a hydrophobic core of the polymer dot, the hydrophilic regions of the fluorescent polymer and the amphiphilic molecule form a hydrophilic outer layer, and the hydrophilic functional group in the fluorescent polymer is located in the hydrophilic outer layer on the surface of the polymer dot.

In some embodiments, the fluorescent polymer is a heteropolymer. In some embodiments, the heteropolymer comprises at least two different monomers. In certain embodiments, the monomers are boron dipyrromethenes, a boron dipyrromethene derivative, fluorene, a fluorene derivative, benzothiadiazole, a benzothiadiazole derivative, benzoxadiole, and/or a benzoxadiole derivative. In some embodiments, the monomers are:

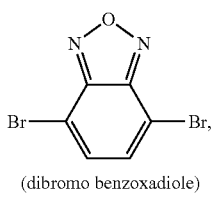

(dibromo benzoxadiole)

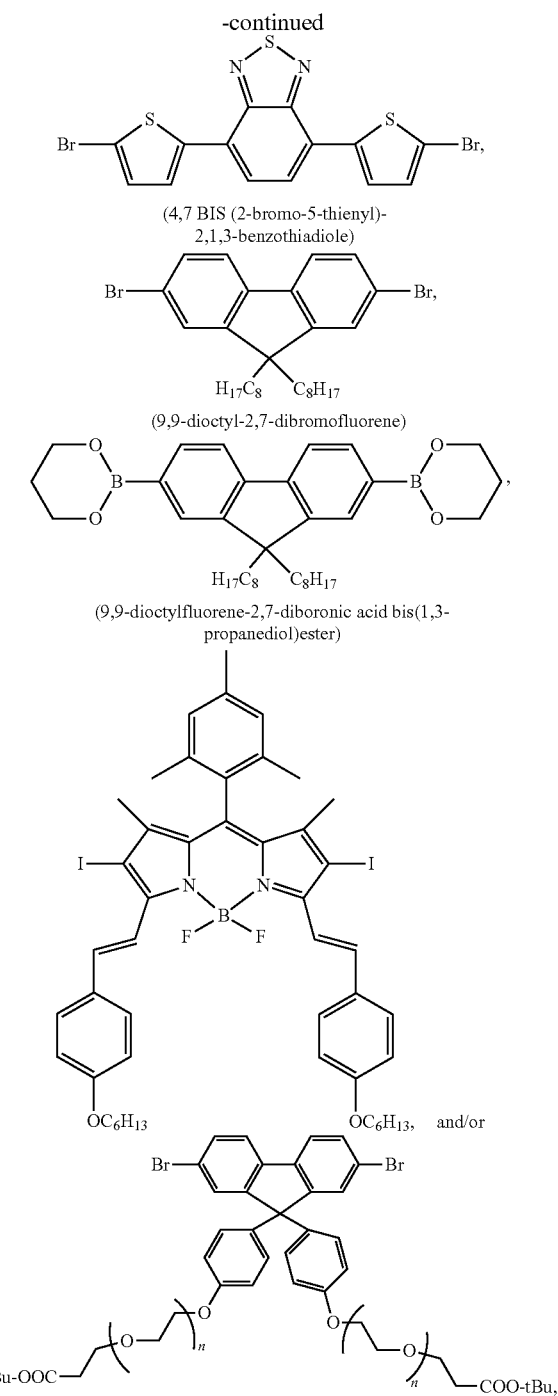

wherein n=10-30. In an embodiment, n=22. In some embodiments, the fluorescent polymer is a homopolymer.

In some embodiments, the hydrophilic functional group is carboxyl, amino, mercapto, azido, alkyne, aldehyde, hydroxyl, carbonyl, sulfate, sulfonate, phosphate, cyanate, succinimidyl ester, strained alkyne, azide, diene, alkene, tetrazine, strained alkene, cyclooctyne, phosphine groups or a derivative thereof. In certain embodiments, the hydrophilic functional group in the polymer is conjugated to a biological molecule. In some embodiments, the biological molecule is a synthetic or naturally occurring protein, a glycoprotein, a polypeptide, an amino acid, a nucleic acid, a carbohydrate, a lipid, or a fatty acid. In some embodiments, the biological molecule is an antibody. In some embodiments, the hydrophilic region of the amphiphilic molecule comprises a polyalkylene glycol. In some embodiments, the polyalkylene glycol is a polyethylene glycol. In some embodiments, the size of the polymer dot is about 5-20 nanometers. In some embodiments, the weight ratio of the amphiphilic molecule to the fluorescent polymer is from about 10% to about 200%. In another embodiment, the weight ratio is expressed as a range of amphiphilic molecule that is between about 0.1 and about 2 to fluorescent polymer (i.e., about 0.1-2.0:1). Some of these embodiments provide weight ratios of about 0.25:1, about 0.5:1, about 0.75:1, about 1:1, about 1.25:1, about 1.5:1, about 1.75:1, or about 2:1. In some embodiments, the hydrophobic region of the amphiphilic molecule comprises a lipid moiety including, but not limited to, 1,2-distearoyl-sn-glycero-3-phosphoethanolamino (DSPE) moiety, 1,2-Dimyristoyl-sn-glycero-3-phosphoethanolamine (DMPE) moiety, 1,2-Dilauroyl-sn-glycero-3-phosphoethanolamine (DLPE) moiety, and (1,2-dipalmitoyl-sn-glycero-3-phosphoethanolamine) (DPPE) moiety. In some embodiments, the amphiphilic molecule is:

1,2-distearoyl-sn-glycero-3-phosphoethanolamine-N-[(polyethylene glycol)-1000 or -2000] (DSPE-PEG);

1,2-distearoyl-sn-glycero-3-phosphoethanolamine-N-poly(ethylene glycol)-Hydroxyl-1000 or -2000] (DSPE-PEG-OH);

1,2-distearoyl-sn-glycero-3-phosphoethanolamine-N-[methoxy(polyethylene glycol)-1000 or -2000] (DSPE-PEG-OCH3), 1,2-distearoyl-sn-glycero-3-phosphoethanolamine-N-[amino(polyethylene glycol)-1000 or -2000] (DSPE-PEG-NH2);

1,2-distearoyl-sn-glycero-3-phosphoethanolamine-N-[carboxy(polyethylene glycol)-1000 or -2000] (DSPE-PEG-COOH);

1,2-distearoyl-sn-glycero-3-phosphoethanolamine-N-[maleimide(polyethylene glycol)-1000 or -2000] (DSPE-PEG-maleimide);

1,2-distearoyl-sn-glycero-3-phosphoethanolamine-N-[biotinyl(polyethylene glycol)-1000 or -2000] (DSPE-PEG-biotin);

1,2-Dimyristoyl-sn-glycero-3-phosphoethanolamine-N-[(polyethylene glycol)-1000 or -2000] (DMPE-PEG);

1,2-Dimyristoyl-sn-glycero-3-phosphoethanolamine-N-[(polyethylene glycol)-Hydroxyl-1000 or -2000] (DMPE-PEG-OH);

1,2-Dimyristoyl-sn-glycero-3-phosphoethanolamine-N-[methoxy(polyethylene glycol)-1000 or -2000] (DMPE-PEG-OCH3);

1,2-Dimyristoyl-sn-glycero-3-phosphoethanolamine-N-[amino(polyethylene glycol)-1000 or -2000] (DMPE-PEG-NH2);

1,2-Dimyristoyl-sn-glycero-3-phosphoethanolamine-N-[carboxy(polyethylene glycol)-1000 or -2000] (DMPE-PEG-COOH);

1,2-Dimyristoyl-sn-glycero-3-phosphoethanolamine-N-[maleimide(polyethylene glycol)-1000 or -2000] (DMPE-PEG-maleimide);

1,2-Dimyristoyl-sn-glycero-3-phosphoethanolamine-N-[biotinyl(polyethylene glycol)-1000 or -2000] (DMPE-PEG-Biotin);

1,2-Dilauroyl-sn-glycero-3-phosphoethanolamine-N-[(polyethylene glycol)-1000 or -2000] (DLPE-PEG);

1,2-Dilauroyl-sn-glycero-3-phosphoethanolamine-N-[(polyethylene glycol)-Hydroxyl-1000 or -2000] (DLPE-PEG-OH);

1,2-Dilauroyl-sn-glycero-3-phosphoethanolamine-N-[methoxy(polyethylene glycol)-1000 or -2000] (DLPE-PEG-OCH3);

1,2-Dilauroyl-sn-glycero-3-phosphoethanolamine-N-[amino(polyethylene glycol)-1000 or -2000] (DLPE-PEG-NH2);

1,2-Dilauroyl-sn-glycero-3-phosphoethanolamine-N-[carboxy(polyethylene glycol)-1000 or -2000] (DLPE-PEG-COOH);

1,2-Dilauroyl-sn-glycero-3-phosphoethanolamine-N-[maleimide(polyethylene glycol)-1000 or -2000] (DLPE-PEG-maleimide);

1,2-Dilauroyl-sn-glycero-3-phosphoethanolamine-N-[biotinyl(polyethylene glycol)-1000 or -2000] (DLPE-PEG-Biotin);

1,2-dipalmitoyl-sn-glycero-3-phosphoethanolamine-N-[(polyethylene glycol)-1000 or -2000] (DPPE-PEG);

1,2-dipalmitoyl-sn-glycero-3-phosphoethanolamine-N-[(polyethylene glycol)-Hydroxyl-1000 or -2000] (DPPE-PEG-OH);

1,2-dipalmitoyl-sn-glycero-3-phosphoethanolamine-N-[methoxy(polyethylene glycol)-1000 or -2000] (DPPE-PEG-OCH3);

1,2-dipalmitoyl-sn-glycero-3-phosphoethanolamine-N-[amino(polyethylene glycol)-1000 or -2000] (DPPE-PEG-NH2);

1,2-dipalmitoyl-sn-glycero-3-phosphoethanolamine-N-[carboxy(polyethylene glycol)-1000 or -2000] (DPPE-PEG-COOH);

1,2-dipalmitoyl-sn-glycero-3-phosphoethanolamine-N-[maleimide(polyethylene glycol)-1000 or -2000] (DPPE-PEG-maleimide);

1,2-dipalmitoyl-sn-glycero-3-phosphoethanolamine-N-[biotinyl(polyethylene glycol)-1000 or -2000] (DPPE-PEG-Biotin);

1,2-distearoyl-sn-glycero-3-phosphoethanolamine-N-[(polyacrylic acid)] (DSPE-PAA);

1,2-distearoyl-sn-glycero-3-phosphoethanolamine-N-[hydroxy(polyacrylic acid)] (DSPE-PAA-OH);

1,2-distearoyl-sn-glycero-3-phosphoethanolamine-N-[methoxy(polyacrylic acid)] (DSPE-PAA-OCH3), 1,2-distearoyl-sn-glycero-3-phosphoethanolamine-N-[amino(polyacrylic acid)] (DSPE-PAA-NH2);

1,2-distearoyl-sn-glycero-3-phosphoethanolamine-N-[carboxy(polyacrylic acid)] (DSPE-PAA-COOH);

1,2-distearoyl-sn-glycero-3-phosphoethanolamine-N-[maleimide(polyacrylic acid)] (DSPE-PAA-maleimide);

1,2-distearoyl-sn-glycero-3-phosphoethanolamine-N-[biotinyl(polyacrylic acid)] (DSPE-PAA-biotin);

1,2-Dimyristoyl-sn-glycero-3-phosphoethanolamine-N-[(polyacrylic acid)] (DMPE-PAA);

1,2-Dimyristoyl-sn-glycero-3-phosphoethanolamine-N-[hydroxy(polyacrylic acid)] (DMPE-PAA-OH);

1,2-Dimyristoyl-sn-glycero-3-phosphoethanolamine-N-[methoxy(polyacrylic acid)] (DMPE-PAA-OCH3);

1,2-Dimyristoyl-sn-glycero-3-phosphoethanolamine-N-[amino(polyacrylic acid)] (DMPE-PAA-NH2);

1,2-Dimyristoyl-sn-glycero-3-phosphoethanolamine-N-[carboxy(polyacrylic acid)] (DMPE-PAA-COOH);

1,2-Dimyristoyl-sn-glycero-3-phosphoethanolamine-N-[maleimide(polyacrylic acid)] (DMPE-PAA-maleimide);

1,2-Dimyristoyl-sn-glycero-3-phosphoethanolamine-N-[biotinyl(polyacrylic acid)] (DMPE-PAA-Biotin);

1,2-Dilauroyl-sn-glycero-3-phosphoethanolamine-N-[(polyacrylic acid)] (DLPE-PAA);

1,2-Dilauroyl-sn-glycero-3-phosphoethanolamine-N-[hydroxy(polyacrylic acid)] (DLPE-PAA-OH);

1,2-Dilauroyl-sn-glycero-3-phosphoethanolamine-N-[methoxy(polyacrylic acid)] (DLPE-PAA-OCH3);
1,2-Dilauroyl-sn-glycero-3-phosphoethanolamine-N-[amino(polyacrylic acid)] (DLPE-PAA-NH2);
1,2-Dilauroyl-sn-glycero-3-phosphoethanolamine-N-[carboxy(polyacrylic acid)] (DLPE-PAA-COOH);
1,2-Dilauroyl-sn-glycero-3-phosphoethanolamine-N-[maleimide(polyacrylic acid)] (DLPE-PAA-maleimide);
1,2-Dilauroyl-sn-glycero-3-phosphoethanolamine-N-[biotinyl(polyacrylic acid)] (DLPE-PAA-Biotin);
1,2-dipalmitoyl-sn-glycero-3-phosphoethanolamine-N-[(polyacrylic acid)] (DPPE-PAA);
1,2-dipalmitoyl-sn-glycero-3-phosphoethanolamine-N-[hydroxy(polyacrylic acid)] (DPPE-PAA-OH);
1,2-dipalmitoyl-sn-glycero-3-phosphoethanolamine-N-[methoxy(polyacrylic acid)] (DPPE-PAA-OCH3); or
1,2-dipalmitoyl-sn-glycero-3-phosphoethanolamine-N-[amino(polyacrylic acid)] (DPPE-PAA-NH2);
1,2-dipalmitoyl-sn-glycero-3-phosphoethanolamine-N-[carboxy(polyacrylic acid)] (DPPE-PAA-COOH);
1,2-dipalmitoyl-sn-glycero-3-phosphoethanolamine-N-[maleimide(polyacrylic acid)] (DPPE-PAA-maleimide);
1,2-dipalmitoyl-sn-glycero-3-phosphoethanolamine-N-[biotinyl(polyacrylic acid)] (DPPE-PAA-Biotin).

In an embodiment, a method for preparing a polymer dot comprises preparing a mixture of a fluorescent polymer and an amphiphilic molecule in an aprotic solvent, wherein the fluorescent polymer comprises hydrophobic regions and hydrophilic regions, the hydrophilic regions having a hydrophilic functional group; and the amphiphilic molecule comprises hydrophobic regions and hydrophilic regions; adding the mixture to a protic solvent to form the polymer dot, wherein the hydrophilic functional group is accessible for conjugation. In some embodiments, the hydrophobic regions of the fluorescent polymer and the amphiphilic molecule are embedded in a hydrophobic core of the polymer dot, the hydrophilic regions of the fluorescent polymer and the amphiphilic molecule form a hydrophilic outer layer, and the hydrophilic functional group in the fluorescent polymer is located in the hydrophilic outer layer on the surface of the polymer dot. In some embodiments, the aprotic solvent is tetrahydrofuran. In certain embodiments, the protic solvent is water. In some embodiments, the method further comprises conjugating a biological molecule to the polymer dot via the hydrophilic functional group.

In an embodiment, a method detecting a target molecule in a biological sample comprises contacting a biological sample with a polymer dot as described above and elsewhere herein.

DETAILED DESCRIPTION

Figure 1:
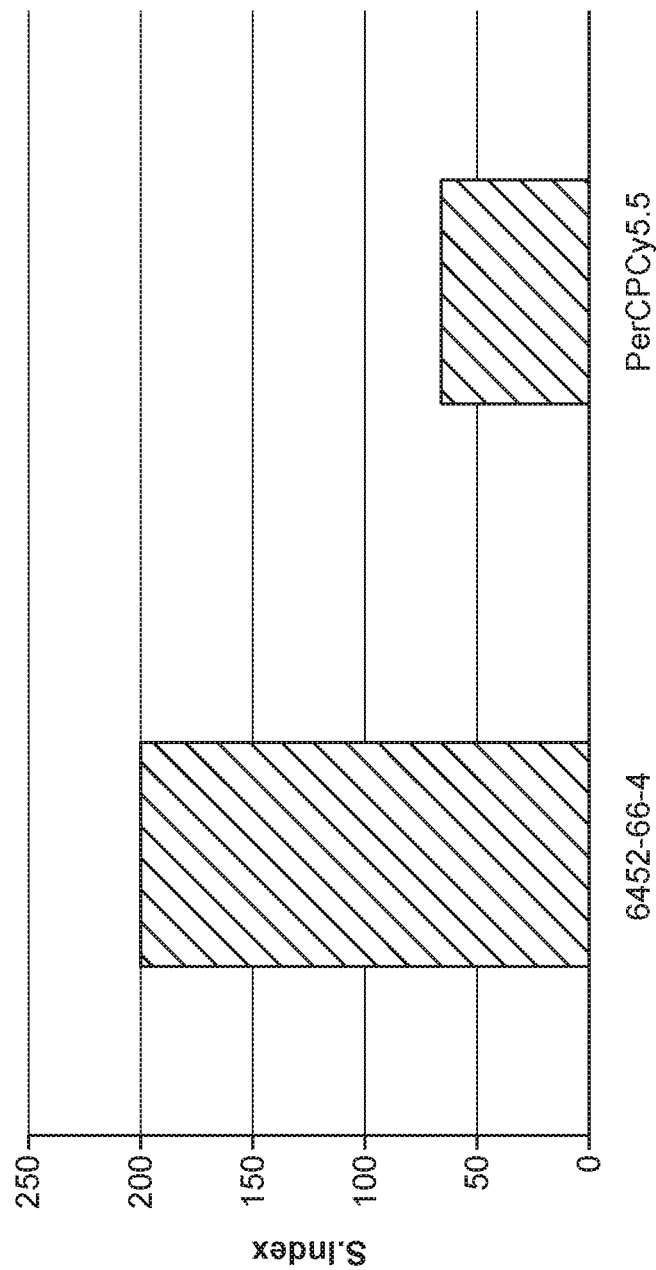
FIG. 1 is a bar graph of the staining index for a polymer dot-anti-CD4 antibody conjugate and a control conjugate.

Described herein are polymer dots, their methods of manufacture, and their biomolecular conjugates. Surface functionalization of the polymer dots is achieved by blending fluorescent polymers bearing functional groups with amphiphilic molecules during manufacture. The polymer dots are stable (e.g., do not aggregate and precipitate out of solution) and can be conjugated to biomolecules due to having surface reactive groups. The conjugates can be used in a large number of different applications including, but not limited to, flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughput screening, cellular imaging, in vivo imaging, fluorescence-based biological assays such as immunoassays and enzyme-based assays, and a variety of fluorescence techniques in biological assays and measurements.

DEFINITIONS

Unless otherwise stated, the following terms used in this application, including the specification and claims, have the definitions given below. As used in this specification and the appended claims, the singular forms "a", "an", and "the" include plural referents unless the content clearly dictates otherwise. Definition of standard chemistry terms can be found in reference works, including Carey and Sundberg (2007) "Advanced Organic Chemistry 5th Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

The term "about" or "approximately" means within an acceptable error range for the particular value as determined by one of ordinary skill in the art, which will depend in part on how the value is measured or determined, i.e., the limitations of the measurement system. The terms "about" and "approximately" are meant to encompass a range of ±25%, ±20%, ±10% or ±5% of a given value. With respect to polymer dot sizes, the terms "about" or "approximately" can indicate that the polymer dot size are of the stated size with a variation of 0-10% around the value (X±10%). Thus, a polymer dot having a diameter of about 20 nm includes polymer dots having a diameter or between 18 and 22 nm. Where the term "about" is used with respect to ratios (e.g., about 0.1:1), it is to be understood that the term "about" applies to both values, specifically, the term applies to both the 0.1 value and the value of 1 in the exemplary ratio.

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0 etc.

As used herein, the term "polymer dot" refers to a structure comprising one or more polymers that have been collapsed into a stable sub-micron sized particle. The polymer dots provided herein may be formed by any method known in the art for collapsing polymers, including without limitation, methods relying on precipitation, methods relying on the formation of emulsions (e.g. mini or micro emulsion), and methods relying on condensation. In some embodiments, the polymer dot is formed by nanoprecipitation.

As used herein, "polymer" is a molecule composed of at least 2 repeating structural units typically connected by covalent chemical bonds. The repeating structural unit may be one type of monomer, and the resulting polymer is a homopolymer. In some embodiments, the polymers can include two different types of monomers, or three different types of monomers, or more types of monomers. The different types of monomers can be distributed along a polymer chain in a variety of ways. For example, three different types of monomers can be randomly distributed along the polymer. The distribution of monomers along the polymer can be represented in different ways. The number of repeating structural units (e.g., monomers) along the length of a polymer can be represented by "n." In some embodiments, n can range, e.g., from at least 2, from at least 100, from at least 500, from at least 1000, from at least 5000, or from at least 10,000, or from at least 100,000, or higher. In certain embodiments, n can range from 2 to 10000, from 20 to 10000, from 20 to 500, from 50 to 300, from 100 to 1000, or from 500 to 10,000. Polymers generally have extended molecular structures comprising backbones that optionally contain pendant side groups. The polymers provided herein can include, but are not limited to, linear polymers and branched polymers.

As used herein, the term "nanoparticle" refers to particles having dimensions less than about 1000 nm.

As used herein, the term "aprotic solvent" refers to a polar solvent which does not contain acidic hydrogen and does not act as a hydrogen bond donor.

As used herein, the term "protic solvent" refers to a solvent that contains a dissociable H+ ion.

As used herein, the term "amphiphilic molecule" or "amphiphilic matrix" refers to a molecule comprising both hydrophobic and hydrophilic segments within the molecule. The term "hydrophilic" in this context refers to the segment of the amphiphilic molecule having a high affinity for aqueous solutions, such as water. The term "hydrophobic" in this context refers to the segment of the amphiphilic molecule that repels aqueous solutions, such as water.

The term "lipid moiety" refers to a moiety comprising at least one lipid. The term "lipid" as used herein refers to small molecules having hydrophobic or amphiphilic properties and include, but are not limited to, fats, waxes, fatty acids, cholesterol, sterols, phospholipids, monoglycerides, diglycerides and triglycerides. The fatty acids can be saturated, mono-unsaturated or poly-unsaturated. Examples of fatty acids include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). The lipid moiety can include several fatty acid groups using branching groups such as lysine and other branched amines.

As used herein, the term "functional group" refers to any chemical unit that can be attached, such as by any stable physical or chemical association, to the fluorescent polymer, thereby altering the surface of the polymer dot, e.g., rendering the surface available for conjugation to a biomolecule (e.g., bioconjugation). The functional group can be covalently linked to a backbone, side chain, or one of the terminating units of the fluorescent polymer. The functional group can be, without limitation, any the following: a aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or a combination thereof. In general, any functional groups that are suitable for bioconjugation may be used. Such functional groups are described, for example, in Bioconjugate Techniques (Academic Press, New York, 2013), which is herein incorporated by reference in its entirety for all purposes.

As used herein, the term "hydrophilic functional group" refers to a functional group that is hydrophilic in nature.

As used herein, the term "derivative" refers to a chemical substance or compound obtained or regarded as derived from another. For examples, a boron dipyrromethene derivative is derived from a boron dipyrromethene.

The term "aliphatic" as used herein refers to an organic compound or radical characterized by a straight chain or branched chain structure, or closed ring structure, any of which may contains saturated carbon bonds, and optionally, one or more unconjugated carbon-carbon unsaturated bonds, such as a carbon-carbon double bond. The aliphatic groups may have from 1 to 24 carbon atoms, e.g., 1, 2, 3, 4, 5, 6, 7, 8, 9, 10, 11, 12, 13, 14, 15, 16, 17, 18, 19, 20, 21, 22, 23, 24 carbon atoms.

As used herein, the term "biomolecule" refers to a synthetic or naturally occurring protein (e.g., an antibody), glycoprotein, peptide, amino acid, metabolite, drug, toxin, nucleic acid, nucleotide, carbohydrate, sugar, lipid, or fatty acid.

"Antibody" refers to an immunoglobulin, composite (e.g., fusion), or fragmentary form thereof. The term includes but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" also includes composite forms including but not limited to fusion proteins having an immunoglobulin moiety. "Antibody" also includes antibody fragments such as Fab, F(ab')2, Fv, scFv, Fd, dAb, Fc, whether or not they retain antigen-binding function.

Polymer Dots

Figure 3:
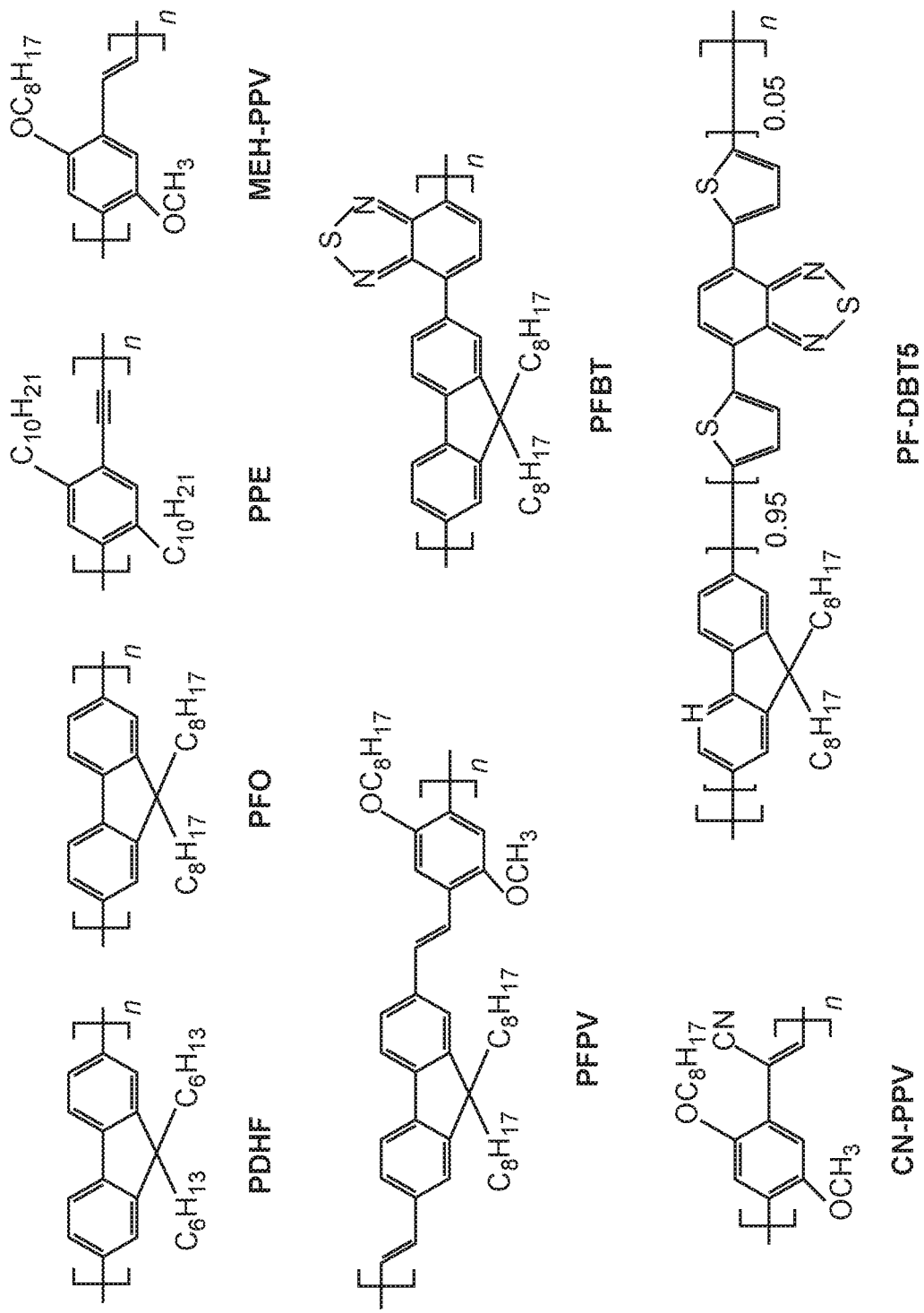
FIG. 3 depicts fluorescent polymers, such as polyfluorene (such as PDHF and PFO), poly(phenylene ethynylene) (such as PPE), poly(phenylene vinylene) (such as MEH-PPV and CN-PPV), fluorene-based copolymers (such as PFPV, PFBT, and PFDBT5), and related derivatives which are disclosed in Wu and Chiu, Angew. Chem. Int. Ed. 2013, 52:3086-3109, which is hereby incorporated by reference in its entirety).
Figure 4A:
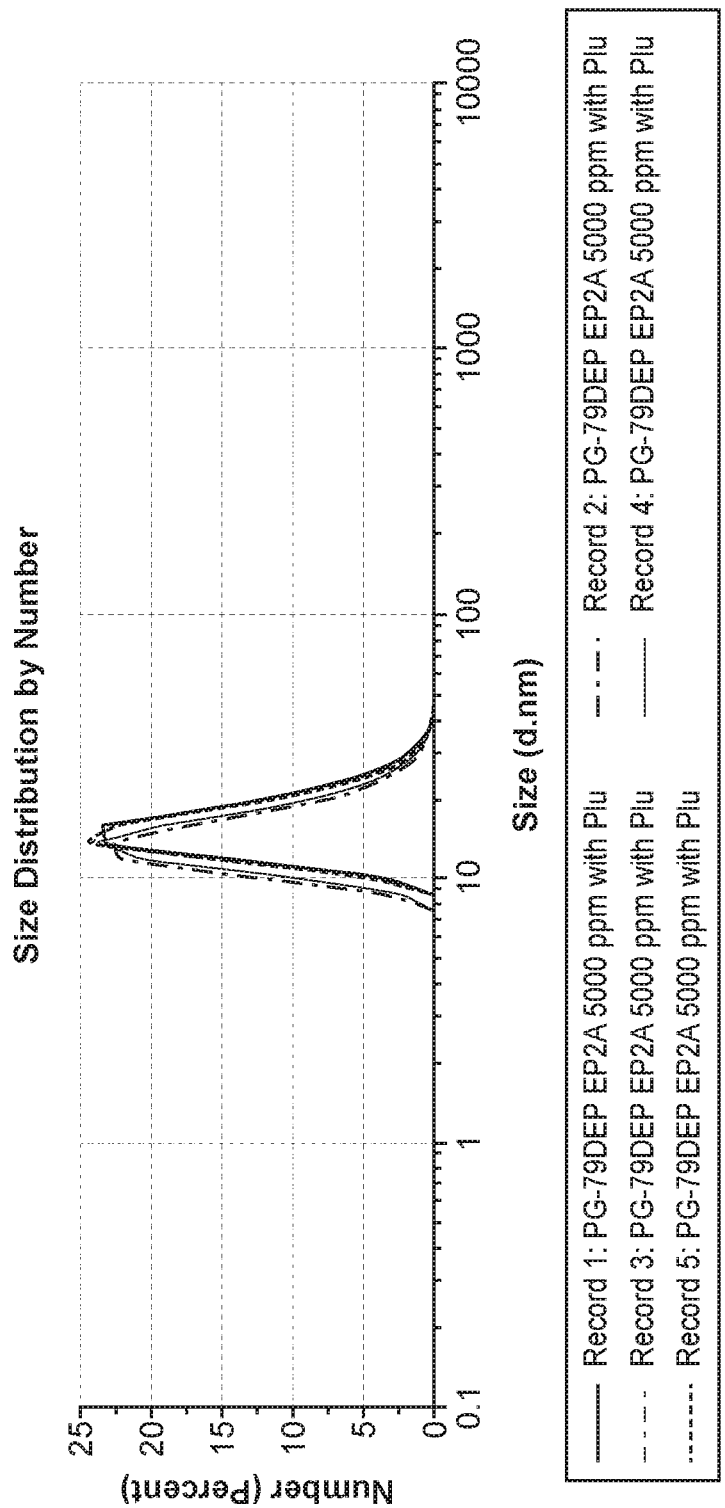
FIGS. 4A-4B show the size distributions of polymer dots produced by the disclosed methods (P-dot 488/700 (FIG. 4A) and P-dot 405/610 (FIG. 4B)). As illustrated in the Figures, more than 50% of the particles have an average effective diameter that is less than or equal to about 25 nm.
Figure 4B:
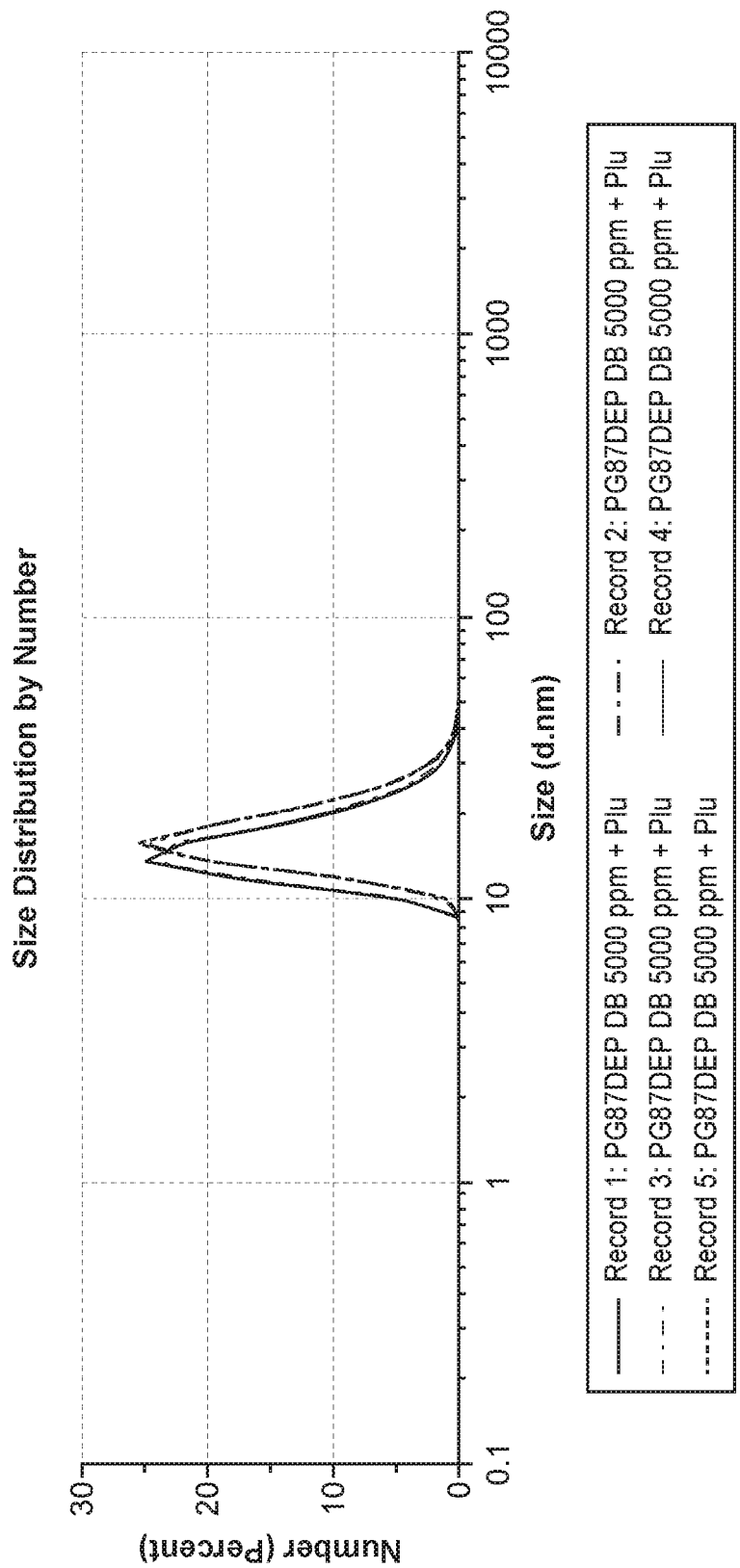

In an embodiment, a polymer dot comprises a fluorescent polymer having hydrophobic regions and hydrophilic regions, the hydrophilic regions contain a hydrophilic functional group. The polymer dot further comprises an amphiphilic molecule having hydrophobic regions and hydrophilic regions. The hydrophobic regions of the fluorescent polymer and the amphiphilic molecule are embedded in a hydrophobic core of the polymer dot, the hydrophilic regions of the fluorescent polymer and the amphiphilic molecule form a hydrophilic outer layer, and the hydrophilic functional group in the fluorescent polymer is located in the hydrophilic outer layer on the surface of the polymer dot. By being localized at the surface of the polymer dot, the hydrophilic functional group is available for attachment to a biomolecule. In certain embodiments, the fluorescent polymer is conjugated and comprises a π-electron delocalized backbone. The fluorescent polymer can be partially or fully conjugated. The term "fluorescent polymer" as used herein refers to a polymer that displays fluorescent properties. Non-limiting examples of fluorescent polymers include polyfluorene (such as PDHF and PFO), poly(phenylene ethynylene) (such as PPE), poly(phenylene vinylene) (such as MEH-PPV and CN-PPV), fluorene-based copolymers (such as PFPV, PFBT, and PFDBT5), and related derivatives (see FIG. 3, drawn from Wu and Chiu, Angew. Chem. Int. Ed. 2013, 52:3086-3109, which is hereby incorporated by reference in its entirety). Other non-limiting examples of fluorescent polymers include boron dipyrromethenes containing polymers and boron dipyrromethene monomers that form such polymers which are disclosed in Rong et al., ACS Nano, 2013, 7(1): 376-384, which is hereby incorporated by reference in its entirety.

In an embodiment, the fluorescent polymer is a heteropolymer comprising at least two different monomers. In an embodiment, at least one monomer is fluorescent and at least one monomer is "functionalized" by being attached or linked (e.g., covalently bonded) to a hydrophilic functional group. In an embodiment, the hydrophilic functional group is attached to a side chain of a monomer within the polymeric chain of the fluorescent polymer. In some embodiments, the hydrophilic functional group is attached to a terminal unit of the fluorescent polymer. In certain embodiments, the fluorescent polymer comprises less than about 6 to about 10% monomers linked to a hydrophilic functional group.

Exemplary monomers from which to form the fluorescent polymer include, but are not limited to, boron dipyrromethenes, a boron dipyrromethene derivative, fluorene, a fluorene derivative, benzothiadiazole, a benzothiadiazole derivative, benzoxadiole, and a benzoxadiole derivative. In some embodiments, the heteropolymer comprises at least two different monomers. In some embodiments, the monomers are dibromo benzoxadiole; 4,7 BIS (2-bromo-5-thienyl)-2,1,3-benzothiadiazole; 9,9-dioctyl-2,7-dibromofluorene; 9,9-dioctylfluorene-2,7-diboronic acid bis(1,3-propanediol)ester;

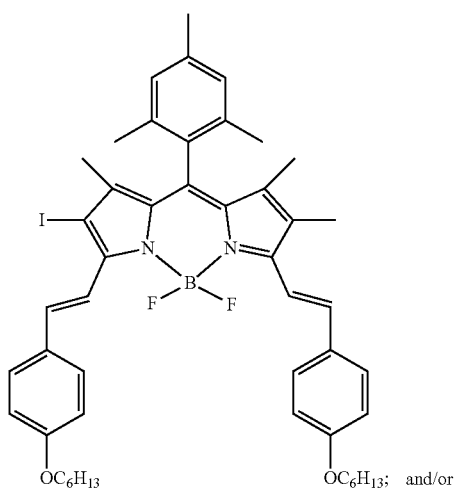

and/or

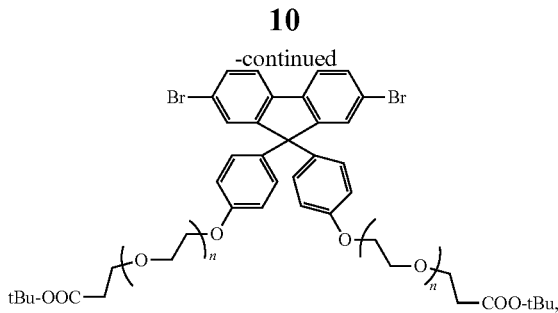

where n=10-30. Having a polymeric side chain in which n=10-30 creates an "arm" that allows the hydrophilic functional group in the fluorescent polymer to be located in the hydrophilic outer layer on the surface of the polymer dot such that the hydrophilic functional group is available for bioconjugation. In an embodiment, n=22.

The amphiphilic molecule helps maintain the water solubility and stability of the polymer dot in solution without causing aggregation for at least about one week, 1 month, 3 months, 6 months, 1 year, 3 years, or 5 years or more. The hydrophobic region of the amphiphilic molecule comprises saturated or unsaturated aliphatic chain moieties having 1-24 carbon atoms, or 1, 2, 3, 4, 5, 6, 7, 8, 9, 10, 11, 12, 13, 14, 15, 16, 17, 18, 19, 20, 21, 22, 23, or 24 carbon atoms. In embodiments, the aliphatic chain moieties form part of a lipid moiety. The lipid moiety includes, but is not limited to, a 1,2-distearoyl-sn-glycero-3-phosphoethanolamino (DSPE) moiety, a 1,2-Dimyristoyl-sn-glycero-3-phosphoethanolamine (DMPE) moiety, a 1,2-Dilauroyl-sn-glycero-3-phosphoethanolamine (DLPE) moiety, or a 1,2-dipalmitoyl-sn-glycero-3-phosphoethanolamine (DPPE) moiety.

The hydrophilic region of the amphiphilic molecule comprises hydrophilic polymers. The hydrophilic polymers include, but are not limited to polyoxyalkylene, polyalkylene glycol, and polycarboxyalkylene. Exemplary hydrophilic polymers include, but are not limited to, polyethylene glycol (PEG), polypropylene glycol, polybutylene glycol, polycarboxymethylene, polycarboxyethylene (or polyacrylic acid (PAA)), polycarboxypropylene and polycarboxybutylene.

In some embodiments, the molecular weight of PEG ranges from about 800 to about 5000, or about 800 to about 4800, or about 800 to about 4600, or about 800 to about 4400, or about 800 to about 4200, or about 800 to about 4000, or about 800 to about 3800, or about 800 to about 3600, or about 800 to about 3400, or about 800 to about 3200, or about 800 to about 3000, or about 800 to about 2800, or about 800 to about 2600, or about 800 to about 2400, or about 800 to about 2200, or about 800 to about 2000, or about 800 to about 1800, or about 800 to about 1600, or about 800 to about 1400, or about 800 to about 1200, or about 800 to about 1000, or about 1000 to about 2000, or about 1000 to about 3000, or about 1000 to about 4000, or about 1000 to about 5000, or about 800, about 1000, about 1200, about 1400, about 1600, or about 1800, about 2000, about 2200, about 2400, about 2600, about 2800, about 3000, about 3200, about 3400, about 3600, about 3800, about 4000, about 4200, about 4400, about 4600, about 4800, about 5000.

Exemplary amphiphilic molecules include, but are not limited to, 1,2-distearoyl-sn-glycero-3-phosphoethanolamine-N-[(polyethylene glycol)-1000 or -2000] (DSPE-PEG);

1,2-distearoyl-sn-glycero-3-phosphoethanolamine-N-poly(ethylene glycol)-Hydroxyl-1000 or -2000] (DSPE-PEG-OH);
1,2-distearoyl-sn-glycero-3-phosphoethanolamine-N-[methoxy(polyethylene glycol)-1000 or -2000] (DSPE-PEG-OCH3);
1,2-distearoyl-sn-glycero-3-phosphoethanolamine-N-[amino(polyethylene glycol)-1000 or -2000] (DSPE-PEG-NH2);
1,2-distearoyl-sn-glycero-3-phosphoethanolamine-N-[carboxy(polyethylene glycol)-1000 or -2000] (DSPE-PEG-COOH);
1,2-distearoyl-sn-glycero-3-phosphoethanolamine-N-[maleimide(polyethylene glycol)-1000 or -2000] (DSPE-PEG-maleimide);
1,2-distearoyl-sn-glycero-3-phosphoethanolamine-N-[biotinyl(polyethylene glycol)-1000 or -2000] (DSPE-PEG-biotin);
1,2-Dimyristoyl-sn-glycero-3-phosphoethanolamine-N-[(polyethylene glycol)-1000 or -2000] (DMPE-PEG);
1,2-Dimyristoyl-sn-glycero-3-phosphoethanolamine-N-[(polyethylene glycol)-Hydroxyl-1000 or -2000] (DMPE-PEG-OH);
1,2-Dimyristoyl-sn-glycero-3-phosphoethanolamine-N-[methoxy(polyethylene glycol)-1000 or -2000] (DMPE-PEG-OCH3);
1,2-Dimyristoyl-sn-glycero-3-phosphoethanolamine-N-[amino(polyethylene glycol)-1000 or -2000] (DMPE-PEG-NH2);
1,2-Dimyristoyl-sn-glycero-3-phosphoethanolamine-N-[carboxy(polyethylene glycol)-1000 or -2000] (DMPE-PEG-COOH);
1,2-Dimyristoyl-sn-glycero-3-phosphoethanolamine-N-[maleimide(polyethylene glycol)-1000 or -2000] (DMPE-PEG-maleimide);
1,2-Dimyristoyl-sn-glycero-3-phosphoethanolamine-N-[biotinyl(polyethylene glycol)-1000 or -2000] (DMPE-PEG-Biotin);
1,2-Dilauroyl-sn-glycero-3-phosphoethanolamine-N-[(polyethylene glycol)-1000 or -2000] (DLPE-PEG);
1,2-Dilauroyl-sn-glycero-3-phosphoethanolamine-N-[(polyethylene glycol)-Hydroxyl-1000 or -2000] (DLPE-PEG-OH);
1,2-Dilauroyl-sn-glycero-3-phosphoethanolamine-N-[methoxy(polyethylene glycol)-1000 or -2000] (DLPE-PEG-OCH3);
1,2-Dilauroyl-sn-glycero-3-phosphoethanolamine-N-[amino(polyethylene glycol)-1000 or -2000] (DLPE-PEG-NH2);
1,2-Dilauroyl-sn-glycero-3-phosphoethanolamine-N-[carboxy(polyethylene glycol)-1000 or -2000] (DLPE-PEG-COOH);
1,2-Dilauroyl-sn-glycero-3-phosphoethanolamine-N-[maleimide(polyethylene glycol)-1000 or -2000] (DLPE-PEG-maleimide);
1,2-Dilauroyl-sn-glycero-3-phosphoethanolamine-N-[biotinyl(polyethylene glycol)-1000 or -2000] (DLPE-PEG-Biotin);
1,2-dipalmitoyl-sn-glycero-3-phosphoethanolamine-N-[(polyethylene glycol)-1000 or -2000] (DPPE-PEG);
1,2-dipalmitoyl-sn-glycero-3-phosphoethanolamine-N-[(polyethylene glycol)-Hydroxyl-1000 or -2000] (DPPE-PEG-OH);
1,2-dipalmitoyl-sn-glycero-3-phosphoethanolamine-N-[methoxy(polyethylene glycol)-1000 or -2000] (DPPE-PEG-OCH3);
1,2-dipalmitoyl-sn-glycero-3-phosphoethanolamine-N-[amino(polyethylene glycol)-1000 or -2000] (DPPE-PEG-NH2);
1,2-dipalmitoyl-sn-glycero-3-phosphoethanolamine-N-[carboxy(polyethylene glycol)-1000 or -2000] (DPPE-PEG-COOH);
1,2-dipalmitoyl-sn-glycero-3-phosphoethanolamine-N-[maleimide(polyethylene glycol)-1000 or -2000] (DPPE-PEG-maleimide);
1,2-dipalmitoyl-sn-glycero-3-phosphoethanolamine-N-[biotinyl(polyethylene glycol)-1000 or -2000] (DPPE-PEG-Biotin);
1,2-distearoyl-sn-glycero-3-phosphoethanolamine-N-[(polyacrylic acid)] (DSPE-PAA);
1,2-distearoyl-sn-glycero-3-phosphoethanolamine-N-[hydroxy(polyacrylic acid)] (DSPE-PAA-OH);
1,2-distearoyl-sn-glycero-3-phosphoethanolamine-N-[methoxy(polyacrylic acid)] (DSPE-PAA-OCH3);
1,2-distearoyl-sn-glycero-3-phosphoethanolamine-N-[amino(polyacrylic acid)] (DSPE-PAA-NH2);
1,2-distearoyl-sn-glycero-3-phosphoethanolamine-N-[carboxy(polyacrylic acid)] (DSPE-PAA-COOH);
1,2-distearoyl-sn-glycero-3-phosphoethanolamine-N-[maleimide(polyacrylic acid)] (DSPE-PAA-maleimide);
1,2-distearoyl-sn-glycero-3-phosphoethanolamine-N-[biotinyl(polyacrylic acid)] (DSPE-PAA-biotin);
1,2-Dimyristoyl-sn-glycero-3-phosphoethanolamine-N-[(polyacrylic acid)] (DMPE-PAA);
1,2-Dimyristoyl-sn-glycero-3-phosphoethanolamine-N-[hydroxy(polyacrylic acid)] (DMPE-PAA-OH);
1,2-Dimyristoyl-sn-glycero-3-phosphoethanolamine-N-[methoxy(polyacrylic acid)] (DMPE-PAA-OCH3);
1,2-Dimyristoyl-sn-glycero-3-phosphoethanolamine-N-[amino(polyacrylic acid)] (DMPE-PAA-NH2);
1,2-Dimyristoyl-sn-glycero-3-phosphoethanolamine-N-[carboxy(polyacrylic acid)] (DMPE-PAA-COOH);
1,2-Dimyristoyl-sn-glycero-3-phosphoethanolamine-N-[maleimide(polyacrylic acid)] (DMPE-PAA-maleimide);
1,2-Dimyristoyl-sn-glycero-3-phosphoethanolamine-N-[biotinyl(polyacrylic acid)] (DMPE-PAA-Biotin);
1,2-Dilauroyl-sn-glycero-3-phosphoethanolamine-N-[(polyacrylic acid)] (DLPE-PAA);
1,2-Dilauroyl-sn-glycero-3-phosphoethanolamine-N-[hydroxy(polyacrylic acid)] (DLPE-PAA-OH);
1,2-Dilauroyl-sn-glycero-3-phosphoethanolamine-N-[methoxy(polyacrylic acid)] (DLPE-PAA-OCH3);
1,2-Dilauroyl-sn-glycero-3-phosphoethanolamine-N-[amino(polyacrylic acid)] (DLPE-PAA-NH2);
1,2-Dilauroyl-sn-glycero-3-phosphoethanolamine-N-[carboxy(polyacrylic acid)] (DLPE-PAA-COOH);
1,2-Dilauroyl-sn-glycero-3-phosphoethanolamine-N-[maleimide(polyacrylic acid)] (DLPE-PAA-maleimide);
1,2-Dilauroyl-sn-glycero-3-phosphoethanolamine-N-[biotinyl(polyacrylic acid)] (DLPE-PAA-Biotin);
1,2-dipalmitoyl-sn-glycero-3-phosphoethanolamine-N-[(polyacrylic acid)] (DPPE-PAA);
1,2-dipalmitoyl-sn-glycero-3-phosphoethanolamine-N-[hydroxy(polyacrylic acid)] (DPPE-PAA-OH);
1,2-dipalmitoyl-sn-glycero-3-phosphoethanolamine-N-[methoxy(polyacrylic acid)] (DPPE-PAA-OCH3);
1,2-dipalmitoyl-sn-glycero-3-phosphoethanolamine-N-[amino(polyacrylic acid)] (DPPE-PAA-NH2);
1,2-dipalmitoyl-sn-glycero-3-phosphoethanolamine-N-[carboxy(polyacrylic acid)] (DPPE-PAA-COOH);
1,2-dipalmitoyl-sn-glycero-3-phosphoethanolamine-N-[maleimide(polyacrylic acid)] (DPPE-PAA-maleimide); and 1,2-dipalmitoyl-sn-glycero-3-phosphoethanolamine-N-[biotinyl(polyacrylic acid)] (DPPE-PAA-Biotin).

In some embodiments, the weight ratio (expressed as w/w %) of amphiphilic molecule to fluorescent polymer ranges from about 10% to about 200%, about 10% to about 175%, about 10% to about 150%, about 10% to about 100%, about 10% to about 75%, or about 100% to about 200%. In some embodiments, the weight ratio of amphiphilic molecule to fluorescent polymer is about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, or about 200%. In various other embodiments, the weight ratio of amphiphilic molecule to fluorescent polymer ranges from about 40% to about 100% (or about 40%, about 50%, about 60% about 70% about 80%, about 90% or about 100%). These values may also be expressed in decimal format instead of a percentage (e.g., 0.1, 0.25, etc. as indicated in Table 1). In another embodiment, the weight ratio (w/w) is expressed as a range of amphiphilic molecule that is between about 0.1 and about 2 to fluorescent polymer (i.e., about 0.1-2.0:1). Some of these embodiments provide weight ratios of about 0.25:1, about 0.5:1, about 0.75:1, about 1:1, about 1.25:1, about 1.5:1, about 1.75:1, or about 2:1. Weight ratios that are too low result in unstable polymer dots that aggregate while weight ratios that are too high increase the particle size modestly (see Table 1). In some instances, using a higher weight ratio cause problems in downstream processes (e.g., low conjugation yield see Table 6). Table 1 also illustrates various weight ratios of amphiphilic molecule to polymer (e.g., 0.25 mg amphiphilic molecule per mg fluorescent polymer).

In embodiments, the size (average effective diameter) of the polymer dot ranges from about 5 nm to about 25 nm, about 10 nm to about 25 nm, about 10 nm to about 25 nm, or about 15 nm to about 25 nm. In an alternative embodiment, the size of the polymer dot ranges from about 10 nm to about 20 nm, about 10 nm to about 15 nm, or about 15 nm to about 20 nm. In some embodiments, the size of the polymer dot is about 10 nm, about 15 nm, about 20 nm, or about 25 nm. Yet other embodiments provide polymer dots of about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, or about 25 nm in average effective diameter.

In other embodiments, a population of polymer dots formed by the disclosed method have a size (average effective diameter) of about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, or about 25 nm, in which at least 50% of the polymer dots in the population of polymer dots have and average effective diameter that is less than or equal to a stated value. Yet other embodiments provide a population of polymer dots in which a least 50% have an average effective diameter of less than or equal to (≤) about 25 nm and more than at least about 5 nm (e.g., at least 50% of the polymer dots in the population have an average effective diameter that ranges between about 5 nm and about 25 nm). Still other embodiments provide a population of polymer dots in which a least 50% have an average effective diameter of less than or equal to (≤) about 20 nm and more than at least about 5 nm (e.g., at least 50% of the polymer dots in the population have an average effective diameter that ranges between about 5 nm and about 20 nm).

Bioconjugation of Polymer Dots

Also provided are methods of conjugating polymer dots to biomolecules. The biomolecule is conjugated to the surface of the polymer dot via a hydrophilic functional group in the fluorescent polymer used to make the polymer dot. In an embodiment, the biomolecule is an antibody that binds to an antigen on the surface of a cell.

The method used to attach or conjugate the biological molecule to the surface of the polymer dots will depend on the type of functional group located on said surface. For example, attachment of proteins to polymer dot-NH2 or polymer dot-COOH may be through a carboimide-mediated coupling reaction. In an embodiment, the properties of biomolecule-conjugated functionalized polymer dots are not changed upon bioconjugation.

In another aspect, a method of detecting a target molecule in a biological sample comprises contacting the biological sample with a disclosed polymer dot.

Methods of Manufacturing Polymer Dots

Also provided are methods of manufacturing polymer dots. The method comprises preparing a mixture of a fluorescent polymer and an amphiphilic molecule in an aprotic solvent, wherein the fluorescent polymer comprises hydrophobic regions and hydrophilic regions, the hydrophilic regions having a hydrophilic functional group; and the amphiphilic molecule comprises hydrophobic regions and hydrophilic regions.

The next step of the method comprises adding the mixture to a protic solvent to form the polymer dot. In the resultant polymer dot, the hydrophobic regions of the fluorescent polymer and the amphiphilic molecule are embedded in a hydrophobic core of the polymer dot, the hydrophilic regions of the fluorescent polymer and the amphiphilic molecule form a hydrophilic outer layer, and the hydrophilic functional group in the fluorescent polymer is located in the hydrophilic outer layer on the surface of the polymer dot.

Spherically shaped polymer dots are formed when the mixture of fluorescent polymer and amphiphilic molecule in an aprotic solvent is added to a protic solvent. The decrease in hydrophobicity leads to the collapse of the hydrophobic regions of the fluorescent polymer and amphiphilic molecule. The polymer dots thus formed have the hydrophobic regions embedded in the core and hydrophilic regions of the fluorescent polymer and amphiphilic molecule on the outer surface such that the functional groups are available for bioconjugation.

Exemplary aprotic solvents include, but are not limited to, tetrahydrofuran, ether, dichloromethane, acetone, acetonitrile, and dimethylformamide. Exemplary protic solvents include, but are not limited to water, methanol, ethanol, propanol, and butanol.

In some embodiments, the method further comprises controlling the size of the polymer dots by adjusting the initial concentration of the fluorescent polymer in the aprotic solvent. Controlling the size of the polymer dots allows for the use of the polymer dots in certain applications. For example, polymer dots that are about 10 nm to about 20 nm in size can be used in flow cytometry. Other suitably sized polymer dots may be useful in different applications.

In some embodiments, the initial concentration of the fluorescent polymer in the aprotic solvent ranges from about 0.05 mg/mL to about 5.0 mg/mL, about 0.1 to about 1.0 mg/mL, about 0.2 mg/mL to about 1.0 mg/mL, about 0.3 mg/mL to about 1.0 mg/mL, about 0.4 mg/mL to about 1.0 mg/mL, about 0.5 mg/mL to about 1.0 mg/mL, about 0.6 mg/mL to about 1.0 mg/mL, about 0.7 mg/mL to about 1.0 mg/mL, about 0.8 mg/mL to about 1.0 mg/mL, or about 0.9 mg/mL to about 1.0 mg/mL. In some embodiments, the initial concentration of the fluorescent polymer in the aprotic solvent is about 0.05 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, or about 1.0 mg/mL.

In certain embodiments, the method further comprises controlling the stability of the polymer dot by controlling the initial concentration of the amphiphilic molecule in the aprotic solvent.

Various non-limiting embodiments include:

1. A polymer dot comprising:
   a fluorescent polymer having hydrophobic regions and hydrophilic regions, the hydrophilic regions having a hydrophilic functional group; and
   an amphiphilic molecule having hydrophobic regions and hydrophilic regions,
   wherein the hydrophilic functional group is accessible for conjugation.

2. The polymer dot of embodiment 1, wherein the hydrophobic regions of the fluorescent polymer and the amphiphilic molecule are embedded in a hydrophobic core of the polymer dot, the hydrophilic regions of the fluorescent polymer and the amphiphilic molecule form a hydrophilic outer layer, and the hydrophilic functional group in the fluorescent polymer is located in the hydrophilic outer layer on the surface of the polymer dot.

3. The polymer dot of embodiment 1 or 2, wherein the fluorescent polymer is a heteropolymer.

4. The polymer dot of embodiment 3, wherein the heteropolymer comprises at least two different monomers.

5. The polymer dot of embodiment 4, wherein the monomers are each independently selected from the group consisting of boron dipyrromethenes, a boron dipyrromethene BODIPY derivative, fluorene, a fluorene derivative, benzothiadiazole, a benzothiadiazole derivative, benzoxadiole, and a benzoxadiole derivative.

6. The polymer dot of embodiment 5, wherein the monomers are each independently selected from the group consisting of:

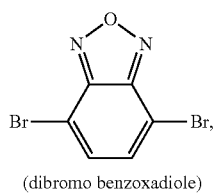

(dibromo benzoxadiole)

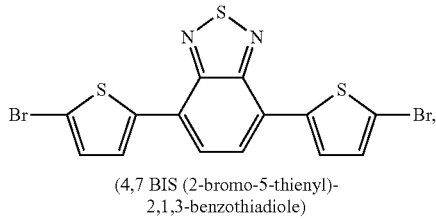

(4,7 BIS (2-bromo-5-thienyl)-2,1,3-benzothiadiole)

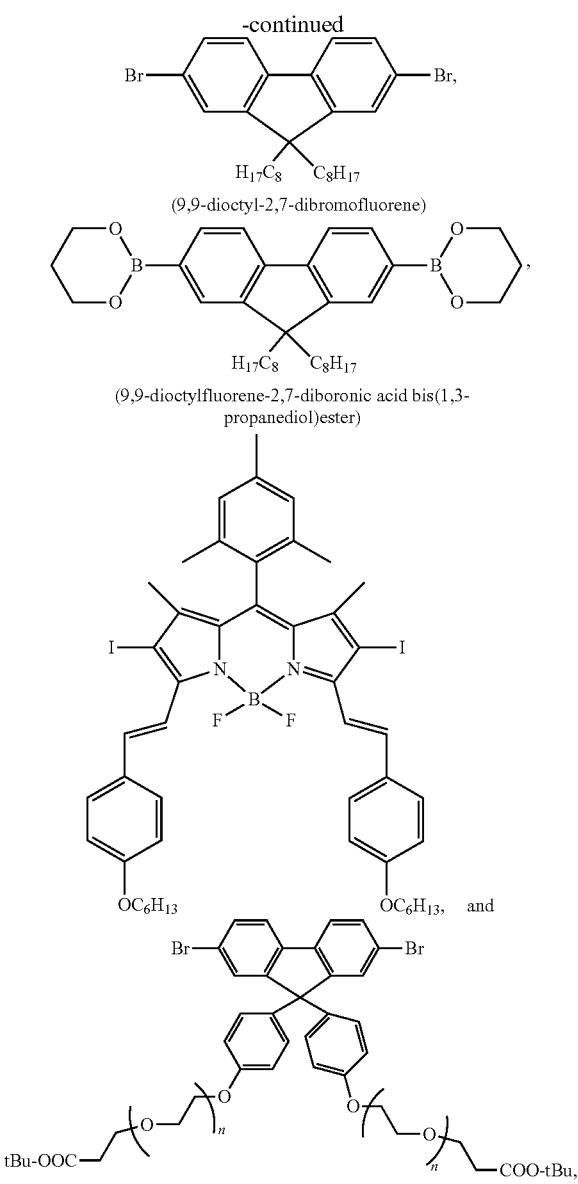

wherein n=10-30.

7. The polymer dot of embodiment 6, wherein n is 22.

8. The polymer dot of any one of embodiments 1-7, wherein the hydrophilic functional group is selected from the group consisting of carboxyl, amino, mercapto, azido, alkyne, aldehyde, hydroxyl, carbonyl, sulfate, sulfonate, phosphate, cyanate, succinimidyl ester, strained alkyne, azide, alkene, tetrazine, strained alkene, cyclooctyne, phosphine groups and a derivative thereof.

9. The polymer dot of any one of embodiments 1-8, wherein the hydrophilic functional group in the polymer is conjugated to a biological molecule.

10. The polymer dot of embodiment 9, wherein the biological molecule is selected from the group consisting of a synthetic or naturally occurring protein, a glycoprotein, a polypeptide, an amino acid, a nucleic acid, a carbohydrate, a lipid, and a fatty acid.

11. The polymer dot of embodiment 9 or 10, wherein the biological molecule is an antibody.

12. The polymer dot of embodiment 1 or 2, wherein the hydrophilic region of the amphiphilic molecule comprises a polyalkylene glycol.

13. The polymer dot of embodiment 12, wherein the polyalkylene glycol is a polyethylene glycol.

14. The polymer dot of any one of embodiments 1-13, wherein the size of the polymer dot is about 5 to about 25 nanometers or about 5 to about 20 nm.

15. The polymer dot of any one of embodiments 1-14, wherein the weight ratio (w/w %) of the amphiphilic molecule to the fluorescent polymer is from about 10% to about 200%.

16. The polymer dot of embodiment 1 or 2, wherein the hydrophobic region of the amphiphilic molecule comprises a lipid moiety selected from the group consisting of 1,2-distearoyl-sn-glycero-3-phosphoethanolamino (DSPE) moiety, 1,2-Dimyristoyl-sn-glycero-3-phosphoethanolamine (DMPE) moiety, 1,2-Dilauroyl-sn-glycero-3-phosphoethanolamine (DLPE) moiety, and (1,2-dipalmitoyl-sn-glycero-3-phosphoethanolamine) (DPPE) moiety.

17. The polymer dot of any one of embodiments 1-16, wherein the amphiphilic molecule is selected from the group consisting of:
1,2-distearoyl-sn-glycero-3-phosphoethanolamine-N-[(polyethylene glycol)-1000 or -2000] (DSPE-PEG);
1,2-distearoyl-sn-glycero-3-phosphoethanolamine-N-poly(ethylene glycol)-Hydroxyl-1000 or -2000] (DSPE-PEG-OH);
1,2-distearoyl-sn-glycero-3-phosphoethanolamine-N-[methoxy(polyethylene glycol)-1000 or -2000] (DSPE-PEG-OCH3);
1,2-distearoyl-sn-glycero-3-phosphoethanolamine-N-[amino(polyethylene glycol)-1000 or -2000] (DSPE-PEG-NH2);
1,2-distearoyl-sn-glycero-3-phosphoethanolamine-N-[carboxy(polyethylene glycol)-1000 or -2000] (DSPE-PEG-COOH);
1,2-distearoyl-sn-glycero-3-phosphoethanolamine-N-[maleimide(polyethylene glycol)-1000 or -2000] (DSPE-PEG-maleimide);
1,2-distearoyl-sn-glycero-3-phosphoethanolamine-N-[biotinyl(polyethylene glycol)-1000 or -2000] (DSPE-PEG-biotin);
1,2-Dimyristoyl-sn-glycero-3-phosphoethanolamine-N-[(polyethylene glycol)-1000 or -2000] (DMPE-PEG);
1,2-Dimyristoyl-sn-glycero-3-phosphoethanolamine-N-[(polyethylene glycol)-Hydroxyl-1000 or -2000] (DMPE-PEG-OH);
1,2-Dimyristoyl-sn-glycero-3-phosphoethanolamine-N-[methoxy(polyethylene glycol)-1000 or -2000] (DMPE-PEG-OCH3);
1,2-Dimyristoyl-sn-glycero-3-phosphoethanolamine-N-[amino(polyethylene glycol)-1000 or -2000] (DMPE-PEG-NH2);
1,2-Dimyristoyl-sn-glycero-3-phosphoethanolamine-N-[carboxy(polyethylene glycol)-1000 or -2000] (DMPE-PEG-COOH);
1,2-Dimyristoyl-sn-glycero-3-phosphoethanolamine-N-[maleimide(polyethylene glycol)-1000 or -2000] (DMPE-PEG-maleimide);
1,2-Dimyristoyl-sn-glycero-3-phosphoethanolamine-N-[biotinyl(polyethylene glycol)-1000 or -2000] (DMPE-PEG-Biotin);
1,2-Dilauroyl-sn-glycero-3-phosphoethanolamine-N-[(polyethylene glycol)-1000 or -2000] (DLPE-PEG);
1,2-Dilauroyl-sn-glycero-3-phosphoethanolamine-N-[(polyethylene glycol)-Hydroxyl-1000 or -2000] (DLPE-PEG-OH);
1,2-Dilauroyl-sn-glycero-3-phosphoethanolamine-N-[methoxy(polyethylene glycol)-1000 or -2000] (DLPE-PEG-OCH3);
1,2-Dilauroyl-sn-glycero-3-phosphoethanolamine-N-[amino(polyethylene glycol)-1000 or -2000] (DLPE-PEG-NH2);
1,2-Dilauroyl-sn-glycero-3-phosphoethanolamine-N-[carboxy(polyethylene glycol)-1000 or -2000] (DLPE-PEG-COOH);
1,2-Dilauroyl-sn-glycero-3-phosphoethanolamine-N-[maleimide(polyethylene glycol)-1000 or -2000] (DLPE-PEG-maleimide);
1,2-Dilauroyl-sn-glycero-3-phosphoethanolamine-N-[biotinyl(polyethylene glycol)-1000 or -2000] (DLPE-PEG-Biotin);
1,2-dipalmitoyl-sn-glycero-3-phosphoethanolamine-N-[(polyethylene glycol)-1000 or -2000] (DPPE-PEG);
1,2-dipalmitoyl-sn-glycero-3-phosphoethanolamine-N-[(polyethylene glycol)-Hydroxyl-1000 or -2000] (DPPE-PEG-OH);
1,2-dipalmitoyl-sn-glycero-3-phosphoethanolamine-N-[methoxy(polyethylene glycol)-1000 or -2000] (DPPE-PEG-OCH3);
1,2-dipalmitoyl-sn-glycero-3-phosphoethanolamine-N-[amino(polyethylene glycol)-1000 or -2000] (DPPE-PEG-NH2);
1,2-dipalmitoyl-sn-glycero-3-phosphoethanolamine-N-[carboxy(polyethylene glycol)-1000 or -2000] (DPPE-PEG-COOH);
1,2-dipalmitoyl-sn-glycero-3-phosphoethanolamine-N-[maleimide(polyethylene glycol)-1000 or -2000] (DPPE-PEG-maleimide);
1,2-dipalmitoyl-sn-glycero-3-phosphoethanolamine-N-[biotinyl(polyethylene glycol)-1000 or -2000] (DPPE-PEG-Biotin);
1,2-distearoyl-sn-glycero-3-phosphoethanolamine-N-[(polyacrylic acid)] (DSPE-PAA);
1,2-distearoyl-sn-glycero-3-phosphoethanolamine-N-[hydroxy(polyacrylic acid)] (DSPE-PAA-OH);
1,2-distearoyl-sn-glycero-3-phosphoethanolamine-N-[methoxy(polyacrylic acid)] (DSPE-PAA-OCH3),
1,2-distearoyl-sn-glycero-3-phosphoethanolamine-N-[amino(polyacrylic acid)] (DSPE-PAA-NH2);
1,2-distearoyl-sn-glycero-3-phosphoethanolamine-N-[carboxy(polyacrylic acid)] (DSPE-PAA-COOH);
1,2-distearoyl-sn-glycero-3-phosphoethanolamine-N-[maleimide(polyacrylic acid)] (DSPE-PAA-maleimide);
1,2-distearoyl-sn-glycero-3-phosphoethanolamine-N-[biotinyl(polyacrylic acid)] (DSPE-PAA-biotin);
1,2-Dimyristoyl-sn-glycero-3-phosphoethanolamine-N-[(polyacrylic acid)] (DMPE-PAA);
1,2-Dimyristoyl-sn-glycero-3-phosphoethanolamine-N-[hydroxy(polyacrylic acid)] (DMPE-PAA-OH);
1,2-Dimyristoyl-sn-glycero-3-phosphoethanolamine-N-[methoxy(polyacrylic acid)] (DMPE-PAA-OCH3);
1,2-Dimyristoyl-sn-glycero-3-phosphoethanolamine-N-[amino(polyacrylic acid)] (DMPE-PAA-NH2);
1,2-Dimyristoyl-sn-glycero-3-phosphoethanolamine-N-[carboxy(polyacrylic acid)] (DMPE-PAA-COOH);
1,2-Dimyristoyl-sn-glycero-3-phosphoethanolamine-N-[maleimide(polyacrylic acid)] (DMPE-PAA-maleimide);
1,2-Dimyristoyl-sn-glycero-3-phosphoethanolamine-N-[biotinyl(polyacrylic acid)] (DMPE-PAA-Biotin);
1,2-Dilauroyl-sn-glycero-3-phosphoethanolamine-N-[(polyacrylic acid)] (DLPE-PAA);
1,2-Dilauroyl-sn-glycero-3-phosphoethanolamine-N-[hydroxy(polyacrylic acid)] (DLPE-PAA-OH);

1,2-Dilauroyl-sn-glycero-3-phosphoethanolamine-N-[methoxy(polyacrylic acid)] (DLPE-PAA-OCH3);
1,2-Dilauroyl-sn-glycero-3-phosphoethanolamine-N-[amino(polyacrylic acid)] (DLPE-PAA-NH2);
1,2-Dilauroyl-sn-glycero-3-phosphoethanolamine-N-[carboxy(polyacrylic acid)] (DLPE-PAA-COOH);
1,2-Dilauroyl-sn-glycero-3-phosphoethanolamine-N-[maleimide(polyacrylic acid)] (DLPE-PAA-maleimide);
1,2-Dilauroyl-sn-glycero-3-phosphoethanolamine-N-[biotinyl(polyacrylic acid)] (DLPE-PAA-Biotin);
1,2-dipalmitoyl-sn-glycero-3-phosphoethanolamine-N-[(polyacrylic acid)] (DPPE-PAA);
1,2-dipalmitoyl-sn-glycero-3-phosphoethanolamine-N-[hydroxy(polyacrylic acid)] (DPPE-PAA-OH);
1,2-dipalmitoyl-sn-glycero-3-phosphoethanolamine-N-[methoxy(polyacrylic acid)] (DPPE-PAA-OCH3); and
1,2-dipalmitoyl-sn-glycero-3-phosphoethanolamine-N-[amino(polyacrylic acid)] (DPPE-PAA-NH2);
1,2-dipalmitoyl-sn-glycero-3-phosphoethanolamine-N-[carboxy(polyacrylic acid)] (DPPE-PAA-COOH);
1,2-dipalmitoyl-sn-glycero-3-phosphoethanolamine-N-[maleimide(polyacrylic acid)] (DPPE-PAA-maleimide);
1,2-dipalmitoyl-sn-glycero-3-phosphoethanolamine-N-[biotinyl(polyacrylic acid)] (DPPE-PAA-Biotin).

18. A method for preparing a polymer dot, the method comprising:
preparing a mixture of an amphiphilic molecule and a fluorescent polymer in an aprotic solvent, wherein the fluorescent polymer comprises hydrophobic regions and hydrophilic regions, the hydrophilic regions having a hydrophilic functional group, the amphiphilic molecule comprises hydrophobic regions and hydrophilic regions and the weight ratio (w/w) of amphiphilic molecule to fluorescent polymer (amphiphilic molecule:fluorescent polymer) is between 0.1 to 2:1 or between about 10% and about 200%;
adding the mixture to a protic solvent to form the polymer dot,
wherein the hydrophilic functional group is accessible for conjugation.

19. The method of embodiment 18, wherein the hydrophobic regions of the fluorescent polymer and the amphiphilic molecule are embedded in a hydrophobic core of the polymer dot, the hydrophilic regions of the fluorescent polymer and the amphiphilic molecule form a hydrophilic outer layer, and the hydrophilic functional group in the fluorescent polymer is located in the hydrophilic outer layer on the surface of the polymer dot.

20. The method of embodiment 18 or 19, wherein the aprotic solvent is tetrahydrofuran.

21. The method of embodiment 18 or 19, wherein the protic solvent is water.

22. The method of any one of embodiments 18-21, further comprising conjugating a biological molecule to the polymer dot via the hydrophilic functional group.

23. The method of any one of embodiments 18-22, wherein the amphiphilic molecule is selected from the group consisting of:
1,2-distearoyl-sn-glycero-3-phosphoethanolamine-N-[(polyethylene glycol)-1000 or -2000] (DSPE-PEG);
1,2-distearoyl-sn-glycero-3-phosphoethanolamine-N-poly(ethylene glycol)-Hydroxyl-1000 or -2000] (DSPE-PEG-OH);
1,2-distearoyl-sn-glycero-3-phosphoethanolamine-N-[methoxy(polyethylene glycol)-1000 or -2000] (DSPE-PEG-OCH3);
1,2-distearoyl-sn-glycero-3-phosphoethanolamine-N-[amino(polyethylene glycol)-1000 or -2000] (DSPE-PEG-NH2);
1,2-distearoyl-sn-glycero-3-phosphoethanolamine-N-[carboxy(polyethylene glycol)-1000 or -2000] (DSPE-PEG-COOH);
1,2-distearoyl-sn-glycero-3-phosphoethanolamine-N-[maleimide(polyethylene glycol)-1000 or -2000] (DSPE-PEG-maleimide);
1,2-distearoyl-sn-glycero-3-phosphoethanolamine-N-[biotinyl(polyethylene glycol)-1000 or -2000] (DSPE-PEG-biotin);
1,2-Dimyristoyl-sn-glycero-3-phosphoethanolamine-N-[(polyethylene glycol)-1000 or -2000] (DMPE-PEG);
1,2-Dimyristoyl-sn-glycero-3-phosphoethanolamine-N-[(polyethylene glycol)-Hydroxyl-1000 or -2000] (DMPE-PEG-OH);
1,2-Dimyristoyl-sn-glycero-3-phosphoethanolamine-N-[methoxy(polyethylene glycol)-1000 or -2000] (DMPE-PEG-OCH3);
1,2-Dimyristoyl-sn-glycero-3-phosphoethanolamine-N-[amino(polyethylene glycol)-1000 or -2000] (DMPE-PEG-NH2);
1,2-Dimyristoyl-sn-glycero-3-phosphoethanolamine-N-[carboxy(polyethylene glycol)-1000 or -2000] (DMPE-PEG-COOH);
1,2-Dimyristoyl-sn-glycero-3-phosphoethanolamine-N-[maleimide(polyethylene glycol)-1000 or -2000] (DMPE-PEG-maleimide);
1,2-Dimyristoyl-sn-glycero-3-phosphoethanolamine-N-[biotinyl(polyethylene glycol)-1000 or -2000] (DMPE-PEG-Biotin);
1,2-Dilauroyl-sn-glycero-3-phosphoethanolamine-N-[(polyethylene glycol)-1000 or -2000] (DLPE-PEG);
1,2-Dilauroyl-sn-glycero-3-phosphoethanolamine-N-[(polyethylene glycol)-Hydroxyl-1000 or -2000] (DLPE-PEG-OH);
1,2-Dilauroyl-sn-glycero-3-phosphoethanolamine-N-[methoxy(polyethylene glycol)-1000 or -2000] (DLPE-PEG-OCH3);
1,2-Dilauroyl-sn-glycero-3-phosphoethanolamine-N-[amino(polyethylene glycol)-1000 or -2000] (DLPE-PEG-NH2);
1,2-Dilauroyl-sn-glycero-3-phosphoethanolamine-N-[carboxy(polyethylene glycol)-1000 or -2000] (DLPE-PEG-COOH);
1,2-Dilauroyl-sn-glycero-3-phosphoethanolamine-N-[maleimide(polyethylene glycol)-1000 or -2000] (DLPE-PEG-maleimide);
1,2-Dilauroyl-sn-glycero-3-phosphoethanolamine-N-[biotinyl(polyethylene glycol)-1000 or -2000] (DLPE-PEG-Biotin);
1,2-dipalmitoyl-sn-glycero-3-phosphoethanolamine-N-[(polyethylene glycol)-1000 or -2000] (DPPE-PEG);
1,2-dipalmitoyl-sn-glycero-3-phosphoethanolamine-N-[(polyethylene glycol)-Hydroxyl-1000 or -2000] (DPPE-PEG-OH);
1,2-dipalmitoyl-sn-glycero-3-phosphoethanolamine-N-[methoxy(polyethylene glycol)-1000 or -2000] (DPPE-PEG-OCH3);
1,2-dipalmitoyl-sn-glycero-3-phosphoethanolamine-N-[amino(polyethylene glycol)-1000 or -2000] (DPPE-PEG-NH2);
1,2-dipalmitoyl-sn-glycero-3-phosphoethanolamine-N-[carboxy(polyethylene glycol)-1000 or -2000] (DPPE-PEG-COOH);

1,2-dipalmitoyl-sn-glycero-3-phosphoethanolamine-N-[maleimide(polyethylene glycol)-1000 or -2000] (DPPE-PEG-maleimide);
1,2-dipalmitoyl-sn-glycero-3-phosphoethanolamine-N-[biotinyl(polyethylene glycol)-1000 or -2000] (DPPE-PEG-Biotin);
1,2-distearoyl-sn-glycero-3-phosphoethanolamine-N-[(polyacrylic acid)] (DSPE-PAA);
1,2-distearoyl-sn-glycero-3-phosphoethanolamine-N-[hydroxy(polyacrylic acid)] (DSPE-PAA-OH);
1,2-distearoyl-sn-glycero-3-phosphoethanolamine-N-[methoxy(polyacrylic acid)] (DSPE-PAA-OCH3),
1,2-distearoyl-sn-glycero-3-phosphoethanolamine-N-[amino(polyacrylic acid)] (DSPE-PAA-NH2);
1,2-distearoyl-sn-glycero-3-phosphoethanolamine-N-[carboxy(polyacrylic acid)] (DSPE-PAA-COOH);
1,2-distearoyl-sn-glycero-3-phosphoethanolamine-N-[maleimide(polyacrylic acid)] (DSPE-PAA-maleimide);
1,2-distearoyl-sn-glycero-3-phosphoethanolamine-N-[biotinyl(polyacrylic acid)] (DSPE-PAA-biotin);
1,2-Dimyristoyl-sn-glycero-3-phosphoethanolamine-N-[(polyacrylic acid)] (DMPE-PAA);
1,2-Dimyristoyl-sn-glycero-3-phosphoethanolamine-N-[hydroxy(polyacrylic acid)] (DMPE-PAA-OH);
1,2-Dimyristoyl-sn-glycero-3-phosphoethanolamine-N-[methoxy(polyacrylic acid)] (DMPE-PAA-OCH3);
1,2-Dimyristoyl-sn-glycero-3-phosphoethanolamine-N-[amino(polyacrylic acid)] (DMPE-PAA-NH2);
1,2-Dimyristoyl-sn-glycero-3-phosphoethanolamine-N-[carboxy(polyacrylic acid)] (DMPE-PAA-COOH);
1,2-Dimyristoyl-sn-glycero-3-phosphoethanolamine-N-[maleimide(polyacrylic acid)] (DMPE-PAA-maleimide);
1,2-Dimyristoyl-sn-glycero-3-phosphoethanolamine-N-[biotinyl(polyacrylic acid)] (DMPE-PAA-Biotin);
1,2-Dilauroyl-sn-glycero-3-phosphoethanolamine-N-[(polyacrylic acid)] (DLPE-PAA);
1,2-Dilauroyl-sn-glycero-3-phosphoethanolamine-N-[hydroxy(polyacrylic acid)] (DLPE-PAA-OH);
1,2-Dilauroyl-sn-glycero-3-phosphoethanolamine-N-[methoxy(polyacrylic acid)] (DLPE-PAA-OCH3);
1,2-Dilauroyl-sn-glycero-3-phosphoethanolamine-N-[amino(polyacrylic acid)] (DLPE-PAA-NH2);
1,2-Dilauroyl-sn-glycero-3-phosphoethanolamine-N-[carboxy(polyacrylic acid)] (DLPE-PAA-COOH);
1,2-Dilauroyl-sn-glycero-3-phosphoethanolamine-N-[maleimide(polyacrylic acid)] (DLPE-PAA-maleimide);
1,2-Dilauroyl-sn-glycero-3-phosphoethanolamine-N-[biotinyl(polyacrylic acid)] (DLPE-PAA-Biotin);
1,2-dipalmitoyl-sn-glycero-3-phosphoethanolamine-N-[(polyacrylic acid)] (DPPE-PAA);
1,2-dipalmitoyl-sn-glycero-3-phosphoethanolamine-N-[hydroxy(polyacrylic acid)] (DPPE-PAA-OH);
1,2-dipalmitoyl-sn-glycero-3-phosphoethanolamine-N-[methoxy(polyacrylic acid)] (DPPE-PAA-OCH3); and
1,2-dipalmitoyl-sn-glycero-3-phosphoethanolamine-N-[amino(polyacrylic acid)] (DPPE-PAA-NH2);
1,2-dipalmitoyl-sn-glycero-3-phosphoethanolamine-N-[carboxy(polyacrylic acid)] (DPPE-PAA-COOH);
1,2-dipalmitoyl-sn-glycero-3-phosphoethanolamine-N-[maleimide(polyacrylic acid)] (DPPE-PAA-maleimide);
1,2-dipalmitoyl-sn-glycero-3-phosphoethanolamine-N-[biotinyl(polyacrylic acid)] (DPPE-PAA-Biotin).

24. The method of an one of embodiments 18-23, wherein the weight ratio of amphiphilic molecule to fluorescent polymer (expressed as a percentage) is about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, or about 200%.

25. The method of any one of embodiments 18-23, wherein the weight ratio of amphiphilic molecule to fluorescent polymer is about 0.1:1, 0.2:1, 0.3:1, 0.4:1, 0.5:1, 0.6:1, 0.7:1, 0.8:1, 0.9:1, 1.0:1, 1.1:1, 1.2:1, 1.3:1, 1.4:1, 1.5:1, 1.6:1, 1.7:1, 1.8:1, 1.9:1, or 2.0:1.

26. A population of polymer dots produced by the method according to any one of embodiments 18-25, said population of polymer dots having an average effective diameter between about 5 nm and about 25 nm, provided that at least 50% of the polymer dots in said population have an average effective diameter of less than about 25 nm.

27. A method of detecting a target molecule in a biological sample, the method comprising contacting a biological sample with the polymer dot of any one of embodiments 1-17 or the population of polymer dots of embodiment 26 and detecting the target molecule.

28. The polymer dot of any one of embodiments 1-17, said polymer dot having an average effective diameter between about 5 nm and about 25 nm, provided that at least 50% of the polymer dots in said population have an average effective diameter of less than about 25 nm.

29. The polymer dot of embodiment 1 or 2, wherein the fluorescent polymer is a homopolymer.

EXAMPLES

The following examples are provided by way of illustration only and not by way of limitation. Those of skill in the art will readily recognize a variety of non-critical parameters that could be changed or modified to yield essentially the same or similar results.

Example 1—Determination of Optimum Ratio of DSPE-PEG-OH to Polymer 700

Polymer 700 was dissolved in 50 mL unstabilized tetrahydrofuran (THF) to make a 200 ppm polymer solution. Using a 25 mg/mL stock solution of DSPE-PEG-OH Nanosoft Polymers in anhydrous dimethyl sulfoxide, 0.25, 0.5, 0.75, 1.25, 1.5, or 1.75 equivalents by mass of DSPE-PEG-OH was added to the polymer solution to make six different mixtures of the polymer and PEG-lipid. For each mixture, while cooling 100 mL of nanopure water in an ice bath for 30 minutes (temperature=5-6° C.), the mixtures of polymer and PEG-lipid in THF were cooled for 15 minutes (temperature=2-3° C.).

To form the polymer dots, each mixture of polymer and PEG-lipid in THF was injected into 100 mL cold nanopure water by a pump (rate=30 mL/minute) with stirring (rate=11.0-11.2 K rpm). THF in the polymer dot mixtures was evaporated off using a cetriVap vacuum concentrator for 3 hours. This step also removed some water, resulting in about 200 ppm polymer dot solutions.

Batches of polymer dots were concentrated further to 5000 ppm using Corning Spin-X UF Concentrators or Sartorius Vivacell 250 (100 k MWCO PES).

The size of each lot of polymer dot was measured by dynamic light scattering (DLS). The quantum yield (QY) was determined by Photoluminescence QY. Percent yield for the lots of polymer dots was also calculated. Results are given in Table 1. The results show that the ratio of DSPE-PEG-OH to polymer affects the size of the polymer dot. Polymer dots with less than 1.25 mg DSPE-PEG-OH per mg of polymer result in 6-7 nm p-dots (by DLS). However, after concentration to 5000 ppm, these same polymer dots increased in size to 17-20 nm (by DLS). The increase in size is due to aggregate formation, resulting in low yields (44-69%). The quantum yield also decreased for these lots. Adding 1.5 or 1.75 mg DSPE-PEG-OH per mg of polymer caused a slight increase in DLS Size and adds cost to the production of the polymer dot.

TABLE 1

Results of varying ratio of DSPE-PEG-OH to Polymer 700

| mg lipid/mg polymer | ~200 ppm Polymer dot | | | ~5000 ppm Polymer dot | | |
|---|---|---|---|---|---|---|
| | DLS Size (nm) | QY(%) | % Yield | DLS Size (nm) | QY(%) | % Yield |
| 0.25 | 7 | 49 | 79 | 17 | 43 | 44 |
| 0.5 | 6 | 48 | 84 | 20 | 43 | 69 |
| 0.75 | 7 | 48 | 86 | 17 | 46 | 78 |
| 1.25 | 14 | 48 | 87 | 14 | 48 | 83 |
| 1.5 | 12 | 46 | 89 | 14 | 46 | 83 |
| 1.75 | 13 | 49 | 88 | 15 | 49 | 83 |

TABLE 6

Conjugation yield as a function of lipid/polymer ratio (DSPE-PEG-OH to Polymer 610)

| mg lipid/mg polymer | % Loss of Conjugation Yield |
|---|---|
| 0.75 | 33% |
| 1.0 | 25% |
| 1.25 | 50% |

Example 2—Preparation of Polymer Dots with Polymer 700 and DSPE-PEG-OH

Polymer 700 was dissolved in 50 mL unstabilized tetrahydrofuran (THF) to make a 200 ppm polymer solution. Using a 25 mg/mL stock solution of DSPE-PEG-OH (Nanosoft Polymers) in anhydrous dimethyl sulfoxide, 1.25 equivalents by mass of DSPE-PEG-OH was added to the polymer solution to make a mixture of the polymer and PEG-lipid. While cooling 100 mL of nanopure water in an ice bath for 30 minutes (temperature=5-6° C.), the mixture of polymer and PEG-lipid in THF was cooled for 15 minutes (temperature=2-3° C.).

To form the polymer dots, the mixture of polymer and PEG-lipid in THF was injected into the cold nanopure water by a pump (rate=30 mL/minute) with stirring (rate=11.0-11.2 K rpm). THF in the polymer dot mixture was evaporated off using a cetriVap vacuum concentrator for 3 hours. This step also removed some water, resulting in about 200 ppm polymer dot solution.

Some batches of polymer dots were concentrated further to 5000 ppm using Corning Spin-X UF Concentrators (100 k MWCO PES). Alternatively, multiple batches of polymer dots were pooled together and concentrated to 5000 ppm using Sartorius Vivacell 250 (100 k MWCO PES) in preparation for conjugating to a protein.

The size of the polymer dots as measured by dynamic light scattering (DLS) along with the % yield for four different lots of polymer dots is given in Table 2. The results show consistent size from lot to lot. The results also show some loss in yield for three out of the four lots upon concentration to about 5000 ppm.

TABLE 2

Survey of Polymer Dot Lots with Polymer 700 and DSPE-PEG-OH

| Polymer 700 lot | ~200 ppm Polymer dot | | ~5000 ppm Polymer dot | |
|---|---|---|---|---|
| | DLS Size (nm) | % Yield | DLS Size (nm) | % Yield |
| 1 | 14 | 84% | 13 | 79% |
| 2 | 13 | 91% | 15 | 74% |
| 3 | 14 | 92% | 14 | 92% |
| 4 | 14 | 86% | 15 | 78% |

Example 3—Preparation of Polymer Dots with Polymer 460 and DSPE-PEG-OH

In this example, the same method as in Example 2 was used to make polymer dots with a different polymer (Polymer 460).

The size of each lot of polymer dot was measured by dynamic light scattering (DLS). The quantum yield (QY) was determined by Photoluminescence. Percent yield for the lots of polymer dots was also calculated. Results are given in Table 3. The results show consistent size from lot to lot. Percent yield varied from 70% to 91% for the 200 ppm polymer dots. The results also show some loss in yield for all three lots upon concentration to about 5000 ppm. Quantum yield did not change upon concentration to about 5000 ppm.

TABLE 3

Survey of Polymer Dot Lots with Polymer 460 and DSPE-PEG-OH

| Polymer 460 lot | ~200 ppm Polymer dot | | | ~5000 ppm Polymer dot | | |
|---|---|---|---|---|---|---|
| | DLS Size (nm) | QY(%) | % Yield | DLS Size (nm) | QY(%) | % Yield |
| 1 | 14 | 78 | 91 | 15 | 78 | 82 |
| 2 | 15 | 77 | 79 | 14 | 75 | 74 |
| 3 | 17 | 79 | 70 | 14 | 78 | 67 |

Example 4—Preparation of Polymer Dots with Polymer 700 and DSPE-PEG-OCH3

A different type of PEG-lipid was used to make the polymer dots. The same method as in Example 2 was used except that DSPE-PEG-OCH3 was used instead of DSPE-PEG-OH. Also, two different ratios of PEG-lipid to polymer were tested: 1.25 mg or 0.75 mg lipid per mg of polymer.

The size of each lot of polymer dot was measured by dynamic light scattering (DLS). Percent yield for the lots of polymer dots was also calculated. Results are given in Tables 4 and 5 below. The results show similar results with respect to size and yield for both ratios of PEG-lipid to polymer tested, indicating that less DSPE-PEG-OCH3 may be needed to stabilize the polymer dots.

TABLE 4

Polymer Dot Lots with 1.25 mg DSPE-PEG-OCH3 per mg Polymer 700

| Polymer 700 lot | ~200 ppm Polymer dot | | ~5000 ppm Polymer dot | |
|---|---|---|---|---|
| | DLS Size (nm) | % Yield | DLS Size (nm) | % Yield |
| 1 | 16 | 89 | 14 | 84 |
| 2 | 15 | 83 | 16 | 79 |

TABLE 5

Polymer Dot Lots with 0.75 mg DSPE-PEG-OCH3 per mg Polymer 700

| Polymer 700 lot | ~200 ppm Polymer dot | | ~5000 ppm Polymer dot | |
|---|---|---|---|---|
| | DLS Size (nm) | % Yield | DLS Size (nm) | % Yield |
| 1 | 15 | 80 | 15 | 79 |
| 2 | 15 | 90 | 16 | 85 |

Example 5—Conjugation of IgG Antibody to Polymer Dots

The polymer dots from Example 2 were first activated by incubating 250 μl (1.25 mg) of polymer dots in a 1.5 mL Eppendorf tube with 6.3 μl of 250 mM sulfo-NHS (Thermo Fisher) and 3.2 μl of 200 mM EDC (Thermo Fisher) for 30 minutes at room temperature. 3.2 μl of 3M triethanolamine (Sigma-Aldrich) and 3.2 μl of 1M aminoethylmaleimide (Sigma-Aldrich) were then added to the tube, mixed, and the tube was incubated in the dark for 3 hours at room temperature.

Anti-CD4 IgG (Bio-Rad) was activated by adding 2.0 μl of 0.5 M EDTA (Sigma-Aldrich) and 2.0 μl of 10 mg/mL iminothiolane (Thermo Fisher) to 200 μl (1 mg) of anti-CD4 IgG to a 1.5 mL Eppendorf tube. The solution was mixed and incubated for 1 hour at room temperature.

The activated polymer dots were quenched by adding 20 μl of 0.5 M taurine (Sigma-Aldrich) to the polymer dot solution. The polymer dot solution was mixed and incubated in the dark for 15 minutes at room temperature.

Both the activated polymer dots and anti-CD4 IgG were desalted with 40K MWCO spin columns (Thermo Fisher) and absorbance was used to determine the total amount of each desalted product. A 3:1 ratio of polymer dot to IgG was used in the conjugation reaction which was incubated in the dark overnight at 4° C. The conjugation was quenched by adding 1/200 volume of 25% N-ethylmaleimide (Sigma-Aldrich) and incubating in the dark at room temperature for 30 minutes.

Free anti-CD4 antibody was removed from the polymer dot-IgG conjugate by size exclusion chromatography.

Example 6—Characterization of Polymer Dots Conjugated to IgG Versus Control Conjugate by Flow Cytometry Flow cytometry was used to determine how the polymer dot-anti-CD4 IgG conjugate from Example 5 (or test conjugate) compared to a control conjugate (PerCPCy5.5; from BioLegend). A ZE5 Sapphire flow cytometer (Bio-Rad) was used in the experiments.

Staining index was determined for the test and control conjugates. The staining index was calculated with the following equation: (MFIpos-MFIneg)/(2*rSDneg) where MFIpos is median fluorescence intensity of the positive population, MFIneg is median fluorescence intensity of the negative population, and rSDneg is relative standard deviation of the negative population. Referring to FIG. 1, the test conjugate gives a significantly higher staining index (>>2x) than the control conjugate.

Figure 2:
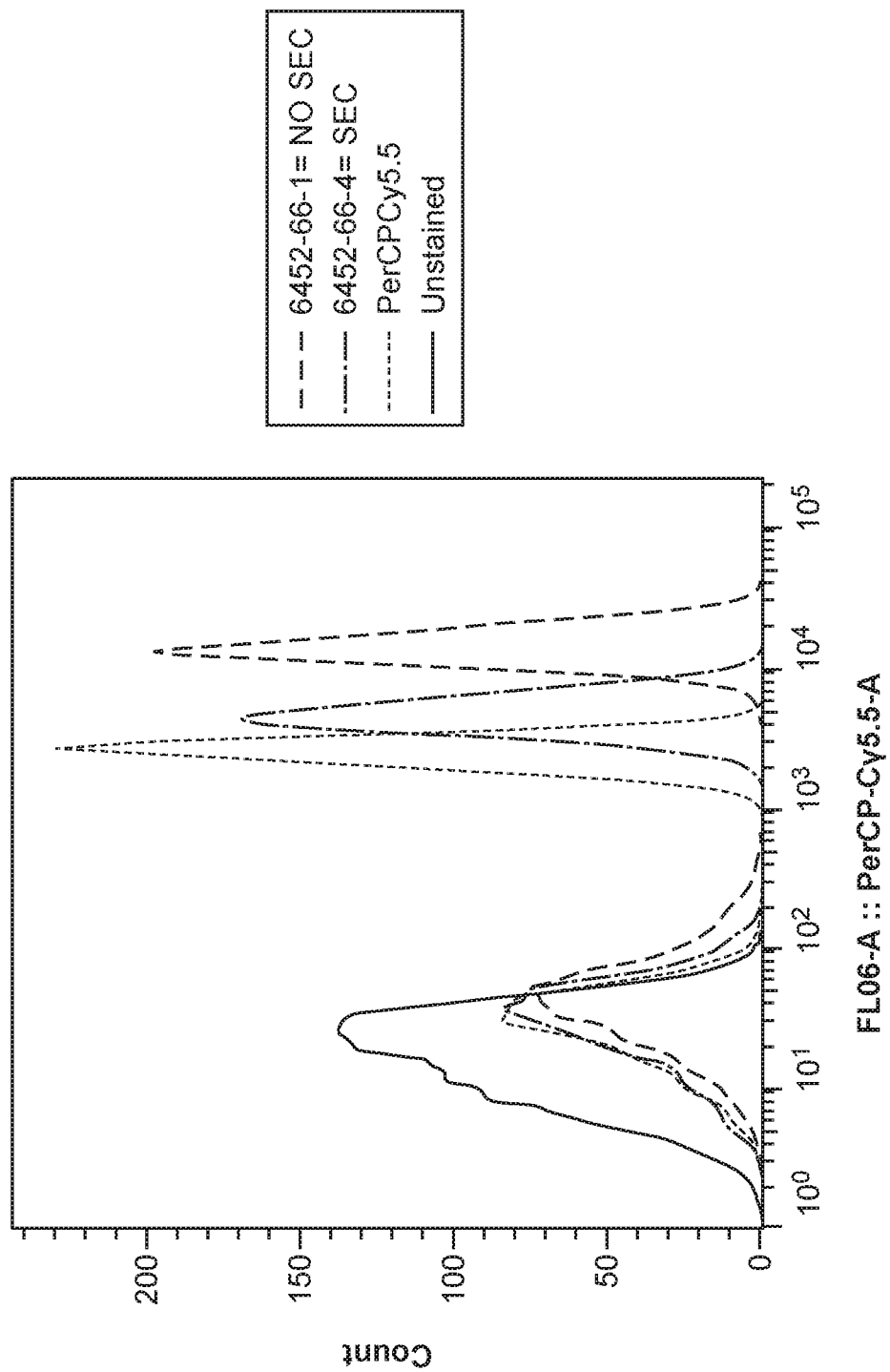
FIG. 2 is histogram plots of positive and negative cell populations for a polymer dot-anti-CD4 antibody conjugate and a control conjugate.

Histogram plots of positive and negative cell populations were obtained for the test (6452-66-1) and control (PerCPCy5.5) conjugate. Results are shown in FIG. 2. For the test conjugate, SEC refers to size exclusion chromatography. The positive peak shape and heights of the positive and negative peaks of the test conjugate were comparable to those of the control conjugate.

Example 7—Effect of PEG-Lipid in P-Dot Stability

Experiment

For each polymer, two sets of small P-dots were made: one containing DSPE-PEG1000-OH (PEG-Lipid), the other without PEG-Lipid. The amount of PEG-Lipid added differs for each Polymer and was been determined previously in a different experiment. Both sets of small P-dots were concentrated to ~5000 ppm. The particles size and yield recovery were evaluated to determine P-dot stability.

Results

| Polymer 488/700 | ~200 ppm P-dot | | ~5000 ppm P-dot | |
|---|---|---|---|---|
| | DLS Size (nm) | % Yield | DLS Size (nm) | % Yield |
| Without PEG-Lipid | 15 | 83% | Aggregated during concentration to ~5000 ppm. | |
| With PEG-Lipid | 14 | 87% | 14 | 83% |

| Polymer 405/610 | ~200 ppm P-dot | | ~5000 ppm P-dot | |
|---|---|---|---|---|
| | DLS Size (nm) | % Yield | DLS Size (nm) | % Yield |
| Without PEG-Lipid | 14 | 63% | Aggregated during concentration to ~5000 ppm. Massive yield loss (12%). | |
| With PEG-Lipid | 15 | 97% | 16 | 92% |

| Polymer 405/790 | ~200 ppm P-dot | | ~5000 ppm P-dot | |
|---|---|---|---|---|
| | DLS Size (nm) | % Yield | DLS Size (nm) | % Yield |
| Without PEG-Lipid | 16 | 61% | Aggregated during concentration to ~5000 ppm. Massive yield loss (24%). | |
| With PEG-Lipid | 16 | 90% | 17 | 89% |

| Polymer | ~200 ppm P-dot | | ~5000 ppm P-dot | |
| --- | --- | --- | --- | --- |
| 405/515 | DLS Size (nm) | % Yield | DLS Size (nm) | % Yield |
| Without PEG-Lipid | 14 | 58% | Aggregated during concentration to ~5000 ppm. Massive yield loss (13%). | |
| With PEG-Lipid | 16 | 80% | 16 | 80% |

Instability of the small P-dots made without PEG-Lipid was already evident even before concentration to 5000 ppm. For polymers 405/610, 405/790 and 405/515, aggregation was observed as early as after the removal of THF. This resulted in lower yields (~60%) in comparison to small P-dots made with PEG-Lipid (80-97%).

It was not possible to concentrate the small P-dots made without PEG-Lipid to 5000 ppm. Aggregates formed and stuck to the membrane of the concentrator, resulting in poor yields (12-24%) which were still dilute (1000-2000 ppm). In contrast, the small P-dots made with PEG-Lipid retained their small particle sizes with little or no step losses.

Example 8—Accelerated Stability Studies

Experimental Methods:

The accelerated shelf life test was conducted at 37° C. Based on the Arrhenius model, with the assumption that the activation energy of the reaction is 15 kcal/mol, 20 days at 37° C. is theoretically equivalent to 1 year at 4° C. (the recommended storage temperature).

P-dots were aliquoted into 7 Eppendorf tubes. Six (6) samples were stored at 37° C. and taken out at different time points. (See Table 7 below.) One (1) sample was stored at 4° C. to serve as a reference.

TABLE 7

| Time | 37° C. (equivalent to months/yrs @ 4° C.) @ 15 kcal/mol |
| --- | --- |
| Day 0 | |
| Day 10 | 6 mos |
| Day 20 | 1 yr |
| Day 40 | 2 yrs |
| Day 60 | 3 yrs |
| Day 80 | 4 yrs |
| Day 100 | 5 yrs |

After removal from the incubation chamber, the sample was examined for aggregates and particle size was also measured. In order to pass the stability test, a sample cannot have aggregates and its particle size has to be within 15% of the particle size of the reference sample.

P-dot 488/700/DSPE-PEG1000-OH—Real Time Stability Data:

| Time | Particle Size from DLS |
| --- | --- |
| t = 0 | 16 nm |
| t = 1.5 yrs | 16 nm |

P-dot 488/700/DSPE-PEG1000-OH—Accelerated Stability Data:

| | | Particle Size from DLS | |
| --- | --- | --- | --- |
| Time | Time Equivalent To | Sample (Stored at 37° C.) | Reference (Stored at 4° C.) |
| t = 0 | t = 0 | 16 | |
| t = 10 d | t = 6 mos | 16 | 16 |
| t = 20 d | t = 1 yr | 16 | 16 |
| t = 40 d | t = 2 yrs | 16 | 16 |
| t = 60 d | t = 3 yrs | 16 | 16 |

P-dot 405/610/DSPE-PEG1000-OH—Accelerated Stability Data:

| | | Particle Size from DLS | |
| --- | --- | --- | --- |
| Time | Time Equivalent To | Sample (Stored at 37° C.) | Reference (Stored at 4° C.) |
| t = 0 | t = 0 | 17 | |
| t = 10 d | t = 6 mos | 16 | 16 |
| t = 20 d | t = 1 yr | 17 | 16 |
| t = 40 d | t = 2 yrs | 17 | 17 |
| t = 60 d | t = 3 yrs | 17 | 17 |
| t = 80 d | t = 4 yrs | 16 | 18 |
| t = 100 d | t = 5 yrs | TBD | TBD |

All patents, patent applications, and other published reference materials cited in this specification are hereby incorporated herein by reference in their entirety.

The invention claimed is:

1. A polymer dot comprising: a) fluorescent polymers that have been collapsed into a stable sub-micron sized particle; and b) amphiphilic molecules, said fluorescent polymers having hydrophobic regions and hydrophilic regions, the hydrophilic regions having a hydrophilic functional group, wherein the hydrophilic functional group is a carboxyl functional group; and said amphiphilic molecule having hydrophobic regions and hydrophilic regions and the hydrophobic region of the amphiphilic molecule comprises a lipid moiety selected from the group consisting of 1,2-distearoyl-sn-glycero-3-phosphoethanolamino (DSPE) moiety, 1,2-Dimyristoyl-sn-glycero-3-phosphoethanolamine (DMPE) moiety, 1,2-Dilauroyl-sn-glycero-3-phosphoethanolamine (DLPE) moiety, and (1,2-dipalmitoyl-sn-glycero-3-phosphoethanolamine) (DPPE) moiety, and wherein the hydrophilic functional group of the fluorescent polymer is accessible for conjugation and the fluorescent polymer is a heteropolymer;

wherein the hydrophobic regions of the fluorescent polymers and the amphiphilic molecules are embedded in a hydrophobic core of the polymer dot, the hydrophilic regions of the fluorescent polymer and the amphiphilic molecule form a hydrophilic outer layer, and the hydrophilic functional group in the fluorescent polymer is located in the hydrophilic outer layer on the surface of the polymer dot; and wherein at least one of the fluorescent polymers comprises

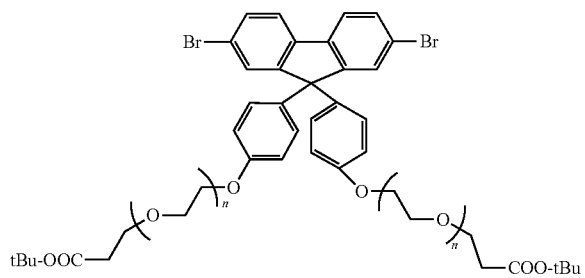

where n=10-30.

2. The polymer dot of claim 1, wherein the heteropolymer comprises at least two different monomers.

3. The polymer dot of claim 2, wherein the monomers are each independently selected from the group consisting of boron dipyrromethenes, a boron dipyrromethene derivative, fluorene, a fluorene derivative, benzothiadiazole, a benzothiadiazole derivative, benzoxadiole, and a benzoxadiole derivative.

4. The polymer dot of claim 3, wherein the monomers are each independently selected from the group consisting of:

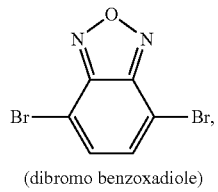

(dibromo benzoxadiole)

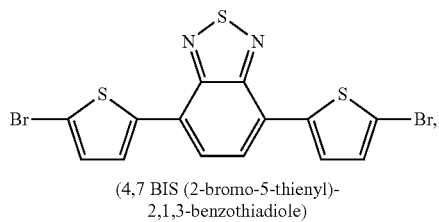

(4,7 BIS (2-bromo-5-thienyl)-2,1,3-benzothiadiole)

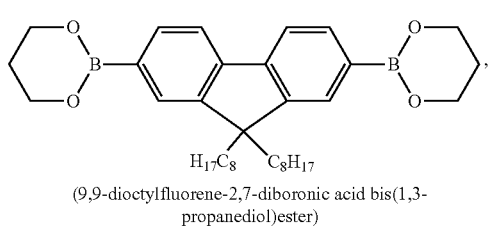

(9,9-dioctylfluorene-2,7-diboronic acid bis(1,3-propanediol)ester)

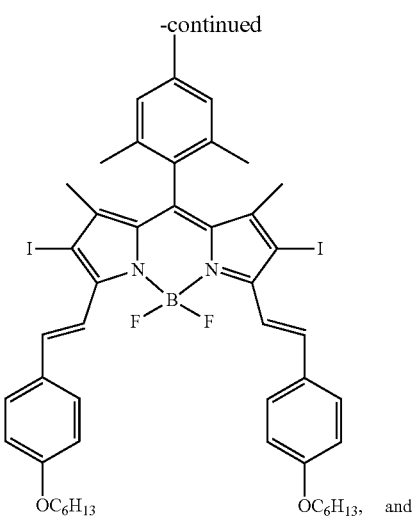

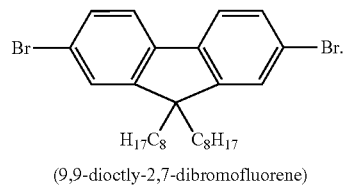

(9,9-dioctly-2,7-dibromofluorene)

5. The polymer dot of claim 4, wherein n is 22.
6. The polymer dot of claim 1, wherein the carboxyl functional group is conjugated to a biological molecule.
7. The polymer dot of claim 6, wherein the biological molecule is selected from the group consisting of a synthetic or naturally occurring protein, a glycoprotein, a polypeptide, an amino acid, a nucleic acid, a carbohydrate, a lipid, and a fatty acid.
8. The polymer dot of claim 7, wherein the naturally occurring protein is an antibody.
9. The polymer dot of claim 1, wherein the hydrophilic region of the amphiphilic molecule comprises a polyalkylene glycol.
10. The polymer dot of claim 9, wherein the polyalkylene glycol is a polyethylene glycol.
11. The polymer dot of claim 1, wherein the size of the polymer dot is about 5 to about 25 nanometers.
12. The polymer dot of claim 1, wherein the weight ratio of the amphiphilic molecule to the fluorescent polymer is about 0.1-2.0:1.
13. The polymer dot of claim 12, wherein the weight ratio of the amphiphilic molecule to the fluorescent polymer is about 1.25:1.
14. The polymer dot of claim 1, wherein the amphiphilic molecule is selected from the group consisting of:
   1,2-distearoyl-sn-glycero-3-phosphoethanolamine-N-[(polyethylene glycol)-1000 or -(DSPE-PEG);
   1,2-distearoyl-sn-glycero-3-phosphoethanolamine-N-poly(ethylene glycol)-Hydroxyl-1000 or -2000] (DSPE-PEG-OH);
   1,2-distearoyl-sn-glycero-3-phosphoethanolamine-N-[methoxy(polyethylene glycol)-1000 or -2000] (DSPE-PEG-OCH$_3$);
   1,2-distearoyl-sn-glycero-3-phosphoethanolamine-N-[amino(polyethylene glycol)-1000 or -2000] (DSPE-PEG-NH$_2$);

1,2-distearoyl-sn-glycero-3-phosphoethanolamine-N-[carboxy(polyethylene glycol)-1000 or -2000] (DSPE-PEG-COOH);

glycol)-1,2-distearoyl-sn-glycero-3-phosphoethanolamine-N-[maleimide(polyethylene glycol)-1000 or -2000] (DSPE-PEG-maleimide);

1,2-distearoyl-sn-glycero-3-phosphoethanolamine-N-[biotinyl(polyethylene glycol)-1000 or -2000] (DSPE-PEG-biotin);

1,2-Dimyristoyl-sn-glycero-3-phosphoethanolamine-N-[(polyethylene glycol)-1000 or -2000] (DMPE-PEG);

1,2-Dimyristoyl-sn-glycero-3-phosphoethanolamine-N-[(polyethylene glycol)-Hydroxyl-1000 or -2000] (DMPE-PEG-OH);

1,2-Dimyristoyl-sn-glycero-3-phosphoethanolamine-N-[methoxy(polyethylene glycol)-1000 or -2000] (DMPE-PEG-OCH$_3$);

1,2-Dimyristoyl-sn-glycero-3-phosphoethanolamine-N-[amino(polyethylene glycol)-1000 or -2000] (DMPE-PEG-NH$_2$);

1,2-Dimyristoyl-sn-glycero-3-phosphoethanolamine-N-[carboxy(polyethylene glycol)-1000 or -2000] (DMPE-PEG-COOH);

1,2-Dimyristoyl-sn-glycero-3-phosphoethanolamine-N-[maleimide(polyethylene glycol)-1000 or -2000] (DMPE-PEG-maleimide);

1,2-Dimyristoyl-sn-glycero-3-phosphoethanolamine-N-[biotinyl(polyethylene glycol)-1000 or -2000] (DMPE-PEG-Biotin);

1,2-Dilauroyl-sn-glycero-3-phosphoethanolamine-N-[(polyethylene glycol)-1000 or -2000] (DLPE-PEG);

1,2-Dilauroyl-sn-glycero-3-phosphoethanolamine-N-[(polyethylene glycol)-Hydroxyl-1000 or -2000] (DLPE-PEG-OH);

1,2-Dilauroyl-sn-glycero-3-phosphoethanolamine-N-[methoxy(polyethylene glycol)-1000 or -2000] (DLPE-PEG-OCH$_3$);

1,2-Dilauroyl-sn-glycero-3-phosphoethanolamine-N-[amino(polyethylene glycol)-1000 or -2000] (DLPE-PEG-NH$_2$);

1,2-Dilauroyl-sn-glycero-3-phosphoethanolamine-N-[carboxy(polyethylene glycol)-1000 or -2000] (DLPE-PEG-COOH);

1,2-Dilauroyl-sn-glycero-3-phosphoethanolamine-N-[maleimide(polyethylene glycol)-1000 or -2000] (DLPE-PEG-maleimide);

1,2-Dilauroyl-sn-glycero-3-phosphoethanolamine-N-[biotinyl(polyethylene glycol)-1000 or -2000] (DLPE-PEG-Biotin);

1,2-dipalmitoyl-sn-glycero-3-phosphoethanolamine-N-[(polyethylene glycol)-1000 or -2000] (DPPE-PEG);

1,2-dipalmitoyl-sn-glycero-3-phosphoethanolamine-N-[(polyethylene glycol)-Hydroxyl-1000 or -2000] (DPPE-PEG-OH);

1,2-dipalmitoyl-sn-glycero-3-phosphoethanolamine-N-[methoxy(polyethylene glycol)-1000 or -2000] (DPPE-PEG-OCH$_3$);

1,2-dipalmitoyl-sn-glycero-3-phosphoethanolamine-N-[amino(polyethylene glycol)-1000 or -2000] (DPPE-PEG-NH$_2$);

1,2-dipalmitoyl-sn-glycero-3-phosphoethanolamine-N-[carboxy(polyethylene glycol)-1000 or -2000] (DPPE-PEG-COOH);

1,2-dipalmitoyl-sn-glycero-3-phosphoethanolamine-N-[maleimide(polyethylene glycol)-1000 or -2000] (DPPE-PEG-maleimide);

1,2-dipalmitoyl-sn-glycero-3-phosphoethanolamine-N-[biotinyl(polyethylene glycol)-1000 or -2000] (DPPE-PEG-Biotin);

1,2-distearoyl-sn-glycero-3-phosphoethanolamine-N-[(polyacrylic acid)] (DSPE-PAA);

1,2-distearoyl-sn-glycero-3-phosphoethanolamine-N-[hydroxy(polyacrylic acid)] (DSPE-PAA-OH);

1,2-distearoyl-sn-glycero-3-phosphoethanolamine-N-[methoxy(polyacrylic acid)] (DSPE-PAA-OCH$_3$), 1,2-distearoyl-sn-glycero-3-phosphoethanolamine-N-[amino(polyacrylic acid)] (DSPE-PAA-NH$_2$);

1,2-distearoyl-sn-glycero-3-phosphoethanolamine-N-[carboxy(polyacrylic acid)] (DSPE-PAA-COOH);

1,2-distearoyl-sn-glycero-3-phosphoethanolamine-N-[maleimide(polyacrylic acid)] (DSPE-PAA-maleimide);

1,2-distearoyl-sn-glycero-3-phosphoethanolamine-N-[biotinyl(polyacrylic acid)] (DSPE-PAA-biotin);

1,2-Dimyristoyl-sn-glycero-3-phosphoethanolamine-N-[(polyacrylic acid)] (DMPE-PAA);

1,2-Dimyristoyl-sn-glycero-3-phosphoethanolamine-N-[hydroxy(polyacrylic acid)] (DMPE-PAA-OH);

1,2-Dimyristoyl-sn-glycero-3-phosphoethanolamine-N-[methoxy(polyacrylic acid)] (DMPE-PAA-OCH$_3$);

1,2-Dimyristoyl-sn-glycero-3-phosphoethanolamine-N-[amino(polyacrylic acid)] (DMPE-PAA-NH$_2$);

1,2-Dimyristoyl-sn-glycero-3-phosphoethanolamine-N-[carboxy(polyacrylic acid)] (DMPE-PAA-COOH);

1,2-Dimyristoyl-sn-glycero-3-phosphoethanolamine-N-[maleimide(polyacrylic acid)] (DMPE-PAA-maleimide);

1,2-Dimyristoyl-sn-glycero-3-phosphoethanolamine-N-[biotinyl(polyacrylic acid)] (DMPE-PAA-Biotin);

1,2-Dilauroyl-sn-glycero-3-phosphoethanolamine-N-[(polyacrylic acid)] (DLPE-PAA);

1,2-Dilauroyl-sn-glycero-3-phosphoethanolamine-N-[hydroxy(polyacrylic acid)] (DLPE-PAA-OH);

1,2-Dilauroyl-sn-glycero-3-phosphoethanolamine-N-[methoxy(polyacrylic acid)] (DLPE-PAA-OCH$_3$);

1,2-Dilauroyl-sn-glycero-3-phosphoethanolamine-N-[amino(polyacrylic acid)] (DLPE-PAA-NH$_2$);

1,2-Dilauroyl-sn-glycero-3-phosphoethanolamine-N-[carboxy(polyacrylic acid)] (DLPE-PAA-COOH);

1,2-Dilauroyl-sn-glycero-3-phosphoethanolamine-N-[maleimide(polyacrylic acid)] (DLPE-PAA-maleimide);

1,2-Dilauroyl-sn-glycero-3-phosphoethanolamine-N-[biotinyl(polyacrylic acid)] (DLPE-PAA-Biotin);

1,2-dipalmitoyl-sn-glycero-3-phosphoethanolamine-N-[(polyacrylic acid)] (DPPE-PAA);

1,2-dipalmitoyl-sn-glycero-3-phosphoethanolamine-N-[hydroxy(polyacrylic acid)] (DPPE-PAA-OH);

1,2-dipalmitoyl-sn-glycero-3-phosphoethanolamine-N-[methoxy(polyacrylic acid)] (DPPE-PAA-OCH$_3$);

1,2-dipalmitoyl-sn-glycero-3-phosphoethanolamine-N-[amino(polyacrylic acid)] (DPPE-PAA-NH$_2$);

1,2-dipalmitoyl-sn-glycero-3-phosphoethanolamine-N-[carboxy(polyacrylic acid)] (DPPE-PAA-COOH);

1,2-dipalmitoyl-sn-glycero-3-phosphoethanolamine-N-[maleimide(polyacrylic acid)] (DPPE-PAA-maleimide); and 1,2-dipalmitoyl-sn-glycero-3-phosphoethanolamine-N-[biotinyl(polyacrylic acid)] (DPPE-PAA-Biotin).

15. A population of polymer dots comprising polymer dots of claim 1, said polymer dots having an average effective diameter between about 5 nm and about 25 nm, provided that at least 50% of the polymer dots in said population have an average effective diameter of less than about 25 nm.

* * * * *